United States Patent

McGarry et al.

Patent Number: 5,216,015
Date of Patent: Jun. 1, 1993

[54] COMPOUNDS HAVING HYPOCHOLESTEROLEMIC PROPERTIES

[75] Inventors: Daniel G. McGarry, King of Prussia; Francis A. Volz, Philadelphia, both of Pa.; John R. Regan, Princeton, N.J.; Michael N. Chang, Newtown, Pa.

[73] Assignee: Rhone-Poulenc Rorer Pharmaceuticals Inc., Collegeville, Pa.

[21] Appl. No.: 650,494

[22] Filed: Feb. 5, 1991

[51] Int. Cl.$^5$ .................. A61K 31/365; C07D 309/30
[52] U.S. Cl. ..................................... 514/460; 549/292
[58] Field of Search .................... 549/292; 514/460

[56] References Cited

U.S. PATENT DOCUMENTS

| | | |
|---|---|---|
| 4,444,784 | 4/1984 | Hoffman et al. |
| 4,661,483 | 4/1987 | Hoffman et al. |
| 4,857,546 | 8/1989 | Duggan et al. |
| 4,863,957 | 9/0589 | Neuenschwande et al. |
| 4,892,884 | 1/1990 | Neuenschwande et al. |
| 4,900,754 | 2/1990 | Regan et al. |
| 4,904,691 | 2/1990 | Neuenschwande et al. |
| 4,904,692 | 2/1990 | Regan et al. |
| 4,939,143 | 7/1990 | Regan et al. |

OTHER PUBLICATIONS

*Proc. Natl. Acad. Sci. USA* vol. 81, pp. 6861-6865, Nov. 1984, Schroepfer et al., 5alpha-Cholest-8(14)-en-3-β-ol-15-one lowers serum cholesterol and induces profound changes in the levels.

*J. Biol. Chem.*, vol. 252, No. 24, Dec. 25, pp. 8975-8980, 1977, Schroepfer et al., Inhibition of Sterol Biosynthesis in L Cells and Mouse Liver Cells by 15-Oxygenated Sterols.

*J. Biol. Chem.*, vol. 240, No. 22, Nov. 25, pp. 7306-14, 1974, Brown et al., Suppression of 3-Hydroxy-3-methylglutaryl Coenzyme A Reductase Activity and Inhibition of.

*J. Biol. Chem.*, vol. 248, No. 24, Dec. 25, pp. 8408-17, 1973, Kandutsch et al., Inhibition of Sterol Synthesis in Cultured Mouse Cells by 7alpha-Hydroxycholesterol, 7β-Hydroxycholesterol, and.

*J. Biol. Chem.*, vol. 249, No. 19, Oct. 10, pp. 6057-61, 1974, Kandutsch et al., Inhibition of Sterol Synthesis in Cultured Mouse Cells by Cholesterol Derivatives Oxygenated in the Side Chain.

Jpn. Kokai Tokkyo Koho JP 01 68,367 [89 68,367], Wakatsuka et al., Bicyclic esters or lactones and analogs as MMG-CoA reductase inhibitors, their preparation, and formulations.

*J. Biol. Chem.*, vol. 257, No. 4, 1929-1936, 1982, Pinkerton et al., 14alpha-Ethyl-5alpha-cholest-7-ene-3β,-15alpha-diol, a Potent Inhibitor of Sterol Biosynthesis, Has Two Sites of.

*J. Biol., Chem.*, vol. 251, No. 6, 1745-1758 (1976), Bell et al., Inhibition of 3-Hydroxy-3-methylglutaryl Coenzyme A Reductase Activity in Hepatoma Tissue.

*Primary Examiner*—C. Warren Ivy
*Assistant Examiner*—Ba K. Trinh
*Attorney, Agent, or Firm*—Paul R. Darkes; Martin F. Savitzky

[57] ABSTRACT

This invention relates to compounds which are steroidyl derivatives of 4-hydroxy-3,4,5,6-tetrahydro-2H-pyran-2-one and the corresponding ring-opened hydroxy acid form thereof which are useful as antihypercholesterolemic agents, to pharmaceutical compositions including such compounds, and to their use in treating hypercholesterolemia.

19 Claims, No Drawings

COMPOUNDS HAVING HYPOCHOLESTEROLEMIC PROPERTIES

BACKGROUND OF THE INVENTION

1. Field of the Invention

The present invention relates to compounds useful for treating cardiovascular disorders in humans or other animals, pharmaceutical compositions including said compounds and to methods for the treatment of cardiovascular disorders using said compounds and pharmaceutical compositions including said compounds. More particularly, the present invention relates to compounds, useful as antihypercholesterolemic agents and methods for reducing serum cholesterol using said compounds and pharmaceutical compositions including said compounds.

Hypercholesterolemia is known to be one of the prime risk factors for atherosclerosis and coronary heart disease, the leading cause of death and disability in Western countries. Although the etiology of atherosclerosis is multifactorial, the development of atherosclerosis and conditions including coronary artery disease, peripheral vascular disease and cerebrovascular disease resulting from restricted blood flow, are associated with abnormalities in serum cholesterol and lipid levels. The etiology of hypercholesterolemia and hyperlipidemia is primarily genetic, although factors such as dietary intake of saturated fats and cholesterol may contribute.

The bile acid sequestrants seem to be moderately effective in treating hypercholesterolemia but they must be consumed in large quantities, i.e., several grams at a time, and they are not very palatable.

Other therapies involve the use of agents which function by limiting cholesterol biosynthesis in the cell. One such therapy involves the use of agents which inhibit the enzyme, 3-hydroxy-3-methylglutaryl coenzyme A reductase (hereinafter HMG-CoA reductase).

2. Reported Developments

Cholesterol derivatives have been reported in the literature to exhibit hypocholesterolemic activity.

5α-cholest-8(14)-en-3β-ol-15-one is reported as having significant hypocholesterolemic acitivity by Schroepfer, et al., *Proc. Natl. Acad. Sci.*, USA 81, 6861–6865 (1984). 5α-cholest-8(14)-en-3β-ol-15-one, 14α-methyl-5α-cholest-7-en-3β-ol-15-one, 3β-methoxy-14α-methyl-5α-cholest-7-en-15β-ol, 3β-methoxy-14α-methyl-5α-cholest-7-en-15α-ol, 5α-cholest-8(14)-en-3β,7ξ,15ξ-triol, 5α-cholest-8(14)-en-3β,15β-diol, 5α-cholest-8(14)-en-3β,15α-diol, 5α,14β-cholest-7-en-3β,15β-diol, 5α,14β-cholest-7-en-3β,15α-diol, 14α-methyl-5α-cholest-7-en-3β,15β-diol, and 14α-methyl-5α-cholest-7-en-3β,15α-diol are reported as potent inhibitors of sterol synthesis by Schroepfer, et al., *J. Biol. Chem.* 252 (24), 8975 (1977). 7-ketocholesterol, along with a series of steroids, is reported to suppress HMG-CoA reductase activity by Brown, et al., *J. Biol. Chem.* 249 (22), 7306 (1974). 7α-hydroxycholesterol, 7β-hydroxycholesterol, and 7-ketocholesterol are reported to inhibit sterol synthesis by Kandutsch, et al., *J. Biol. Chem.* 248 (24), 8408 (1974), as are sterols derived from cholesterol by hydroxylation at the 20α, 22α, 22β, or 25 position, *J. Biol. Chem.* 249 (19), 6057 (1974).

Derivatives of 4-hydroxy-3,4,5,6-tetrahydro-2H-pyran-2-one are reported in the literature as specific competitive HMG-CoA reductase inhibitors.

These derivatives include lovastatin (the active agent in MEVACOR ®), which has the following structure:

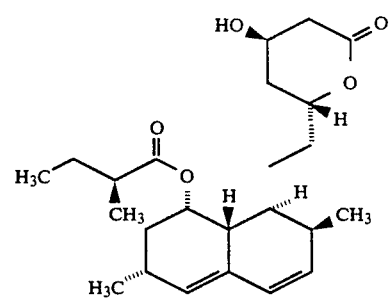

and analogs and homologs thereof.

4-Hydroxy-3,4,5,6-tetrahydro-2H-pyran-2-ones, and the corresponding ring-opened hydroxy acids, described as analogs of lovastatin and related compounds and which contain an aminoalkyl or substituted aminoalkyl group on the 6-position of the polyhydronaphthyl moiety, described as having antihypercholesterolemic properties, are reported in U.S. Pat. No. 4,857,546. Compounds described as semi-synthetic analogs of compactin, mevinolin, hydroxylated compactin and hydroxylated mevinolin and the dihydro and tetrahydro analogs thereof which possess a specifically substituted 8'-ester acyl moiety are reported in U.S. Pat. No. 4,661,483. Antihypercholesterolemic compounds described as 6(R)-[2-(8'-acyloxy-2'-methyl-6'-methyl (or hydrogen)-polyhydronaphthyl-1')-ethyl]-4(R)-hydroxy-3,4,5,6-tetrahydro-2H-pyran-2-ones and their hydroxy acid form are reported in U.S. Pat. No. 4,444,784.

Trans-6-[2-[aryl and arylalkylbicyclo[a.2.b]alk(en)yl]alk(en)yl]-3,4,5,6-tetrahydro-4-hydroxy-2H-pyran-2-ones and the corresponding ring-opened hydroxy acids, are reported as HMG-CoA reductase inhibitors, U.S. Pat. No. 4,904,692, as are trans-6-[(2-aryl substituted cycloalkenyl and substituted cycloalkyl)alkenyl and alkyl]-3,4,5,6-tetrahydro-4-hydroxy-2H-pyran-2-ones and the corresponding ring-opened hydroxy acids, U.S. Pat. Nos. 4,863,957, 4,900,754, and 4,939,143, trans-6-[(2-aryl substituted cycloalkadienyl) alkenyl or alkyl]-3,4,5,6-tetrahydro-4-hydroxy-2H-pyran-2-ones and the corresponding ring-opened hydroxy acids, U.S. Pat. No. 4,892,884, and trans-6-[(2-aryl substituted spirocyclic-1,3-dien-1-yl)alkenyl or alkyl]-3,4,5,6-therahydro-4-hydroxy-2H-pyran-2-ones and the corresponding ring-opened hydroxy acids, U.S. Pat. No. 4,904,691.

6-[(2-oxabicyclo[4.3.0]non-7-yl)alkyl]-4-hydroxy-2H-pyran-2-ones are reported as HMG-CoA reductase inhibitors, Jpn. Kokai Tokkyo Koho JP 01 68,367 [89 68,367].

The present invention relates to novel steroid compounds possessing hypocholesterolemic properties.

SUMMARY OF THE INVENTION

This invention relates to compounds having a steroidyl group with a 5- or 6-membered D ring linked at the 17- or 17a-position, respectively, to the 6-position of 4-hydroxy-3,4,5,6-tetrahydro-2H-pyran-2-one, the corresponding ring-opened hydroxy-acid forms thereof, or pharmaceutically acceptable salts thereof.

Additionally, this invention relates to pharmaceutical compositions including the novel compounds described above and methods for treating hypercholesterolemia and hyperlipidemia, and disease conditions in which hypercholesterolemia is an etiological factor, using said pharmaceutical compositions.

DETAILED DESCRIPTION OF THE INVENTION

As used above and throughout the description of this invention, the following terms, unless otherwise indicated, shall be understood to have the following meanings:

"Alkyl" means a saturated aliphatic hydrocarbon group which may be straight or branched and having about 1 to about 20 carbon atoms in the chain. Branched means that a lower alkyl group such as methyl, ethyl or propyl is attached to a linear alkyl chain. Preferred alkyl groups are the "lower alkyl" groups which are those alkyl groups having from 1 to about 6 carbons.

"Alkoxycarbonyloxy" means an

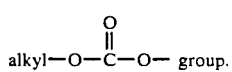

Preferred groups are those in which the alkyl group is lower group.

"Acyl" means an

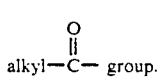

Preferred acyl groups are those in which the alkyl group is lower alkyl.

"Acyloxy" means an

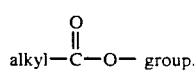

Preferred acyloxy groups are those in which the alkyl group is lower alkyl.

"Alkylamino" means an alkyl-NH- group. Preferred groups are lower alkylamino groups.

"Alkylsulfonyl" means an

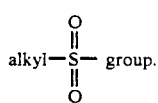

Preferred groups are those in which the alkyl group is lower alkyl.

"Alkylsulfinyl" means an

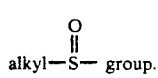

Preferred groups are those in which the alkyl group is lower alkyl.

"Alkylthio" means an alkyl-S- group. Preferred groups are lower alkylthio.

"Alkoxy" means an alkyl-O- group. Lower alkoxy groups are preferred. Exemplary groups include methoxy, ethoxy, n-propoxy, i-propoxy and n-butoxy.

"Aralkyl" means an alkyl group substituted by an aryl radical, wherein "aryl" means a phenyl or phenyl substituted with one or more substituents which may be alkyl, alkoxy, amino, nitro, carboxy, carboalkoxy, cyano, alkylamino, halo, hydroxy, hydroxyalkyl, mercapto, alkylthio, acyl, or carbamoyl. Exemplary groups include benzyl and phenethyl.

"Aralkoxy" means an aralkyl-O- group. Exemplary groups include benzyloxy and phenethyloxy.

"Aralkoxycarbonyloxy" means an

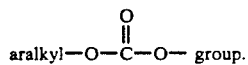

"Aralkylsulfonyl" means an

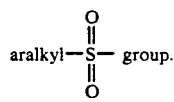

"Aralkylsulfinyl" means an

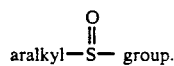

"Aroyloxy means an

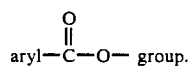

"Aryloxy" means an aryl-O- group. Exemplary groups include phenoxy and 2-naphthyloxy.

"Aryloxycarbonyloxy" means an

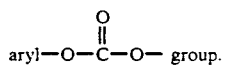

"Aroylamino means an

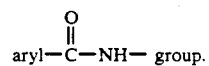

"Arylsulfonyl" means an

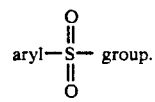

"Arylsulfinyl" means an

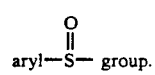

"Carboalkoxy" means an

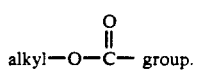

Preferred carboalkoxy groups are those in which the alkyl group is lower alkyl.

"Carboaralkoxy" means an

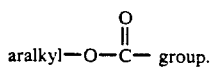

Preferred groups include carbobenzyloxy and carbophenethyloxy.

"Carboaryloxy" means an

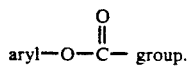

Preferred groups include carbophenoxy and carbo-2-naphthyloxy.

"Dialkylamino" is an

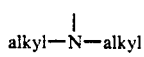

group where the alkyl groups may be the same or different. Preferred dialkylamino groups are those in which the alkyl groups are lower alkyl.

"Linked" means connected by a group Z wherein Z is

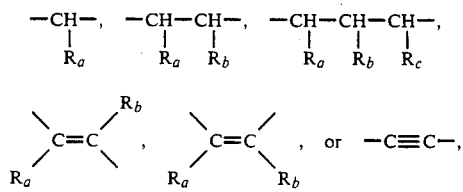

where $R_a$, $R_b$, and $R_c$ are independently hydrogen or lower alkyl.

"Steroidyl group" is a steroid fused ring system known in the prior art or prepared by literature methods from prior art steroids, and capable of being linked to the 4-hydroxy-3,4,5,6-tetrahydro-2H-pyran-2-one moiety as described herein.

The steroid nomenclature used above and throughout the description of this invention is that as described in, for example, "Definitive Rules for Nomenclature of Steroids", *Pure and Applied Chemistry* 31, 285 (1972). The steroids are numbered and the rings are lettered as shown below for steroids containing 5- or 6-membered D rings.

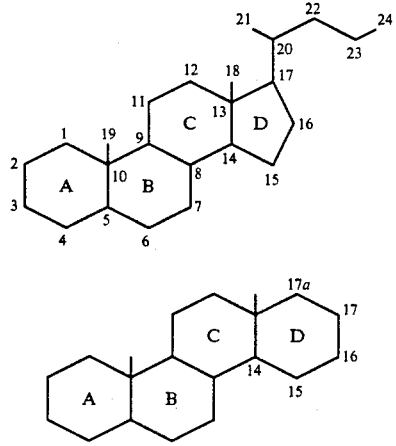

Preferred compounds of the present invention and the corresponding ring-opened hydroxy acid forms thereof are described by Formulae I and II, respectively, below

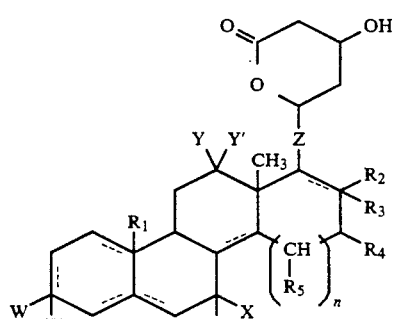

Formula I

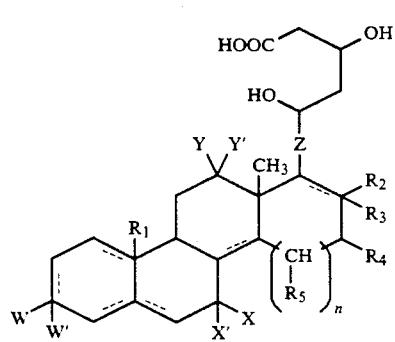

Formula II wherein:

$R_1$ is methyl or part of a double bond;
$R_2$ is hydrogen, alkyl, aryl or aralkyl;
$R_3$ is hydrogen, alkyl or part of a double bond;
$R_2$ and $R_3$ together may form a spiro-group of formula

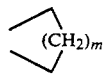

where m is 0–4;
$R_4$ and $R_5$ are independently hydrogen, alkyl, aralkyl or aryl;
W is carboalkoxy, carboaryloxy, carboaralkoxy, hydrogen, hydroxy, alkoxy, aryloxy, aralkoxy, alkoxycarbonyloxy, aryloxycarbonyloxy, aralkoxycarbonyloxy, amino, alkylamino, dialkylamino, aminomethyl, alkylaminomethyl, dialkylaminomethyl, alkylthio, alkylsulfonyl, arylthio, arylsulfonyl, alkysulfonyl, aralkylsulfonyl, alkylsulfinyl, arylsulfinyl, aralkylsulfinyl, acyloxy, aroyloxy, acylamino or aroylamino;
W' is hydrogen or part of a double bond;
W and W' together may form an oxo group provided that the A ring of the steroidyl group is not a phenyl ring and provided further that the A ring of the steroidyl group does not contain a double bond in the 2,3 or 3,4 position;
X is carboalkoxy, carboaryloxy, carboaralkoxy, hydrogen, hydroxy, alkoxy, aryloxy, aralkoxy, alkoxycarbonyloxy, aryloxycarbonyloxy, aralkoxycarbonyloxy, amino, alkylamino, dialkylamino, aminomethyl, alkylaminomethyl, dialkylaminomethyl, alkylthio, alkylsulfonyl, arylthio, arylsulfonyl, alkylsulfonyl, aralkylsulfonyl, alkylsulfinyl, arylsulfinyl, aralkylsulfinyl, acyloxy, aroloxy, acylamino or aroylamino;

X' is hydrogen;

X and X' together may form an oxo group;

Y is carboalkoxy, carboaryloxy, carboaralkoxy, hydrogen, hydroxy, alkoxy, aryloxy, aralkoxy, alkoxycarbonyloxy, aryloxycarbonyloxy, aralkoxycarbonyloxy, amino, alkylamino, dialkylamino, aminomethyl, alkylaminomethyl, dialkylaminomethyl, alkylthio, alkylsulfonyl, arylthio, arylsulfonyl, alkylsulfonyl, aralkylsulfonyl, alkylsulfinyl, arylsulfinyl, aralkylsulfinyl, acylamino, aroylamino or

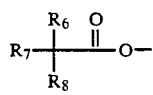

wherein $R_6$, $R_7$ and $R_8$ are independently hydrogen, alkyl, aralkyl or aryl;

Y' is hydrogen;

Y and Y' together may form an oxo group;

Z is

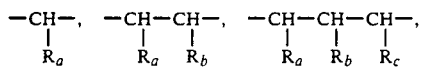

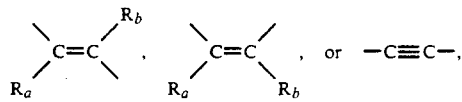

where $R_a$, $R_b$, and $R_c$ are independently hydrogen or lower alkyl; and n is 0 or 1.

It should be understood that ----- indicates that the bond may be a single or double bond. It should be further understood that when the A ring of the steroidyl group is a phenyl ring, or when the A ring of the steroidyl group contains a double bond at the 4,5 position, that the steroidyl group does not also contain a double bond at the 5,6 position.

Another preferred class of compounds of this invention is described by Formulae I and II wherein the A ring of the steroidyl group is a phenyl ring or wherein the A ring is cyclohexyl ring and the B ring contains a double bond at the 5,6 position.

A more preferred class of compounds of this invention is described by Formulae I and II wherein the A ring of the steroidyl group is a cyclohexyl ring or a cyclohexenyl ring with the double bond at the 4,5 position.

A still more preferred class of compounds of this invention is described by Formulae I and II wherein the A ring of the steroidyl group is a cyclohexyl ring.

An even more preferred class of compounds of this invention is described by Formula III below wherein the preferred stereochemistry of the steroidyl group is presented.

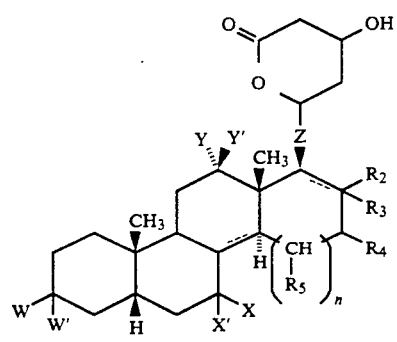

Formula III

Another even more preferred class of compounds of this invention is described by Formula IV below.

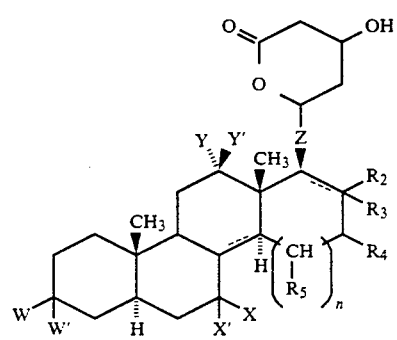

Formula IV

A most preferred class of compounds of this invention is described by Formula V below where the preferred stereochemistry of the 4-hydroxy-3,4,5,6-tetrahydro-2H-pyran-2-one moiety is presented.

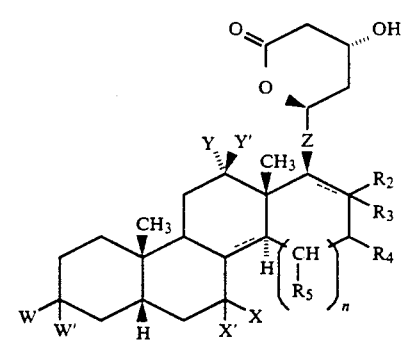

Formula V

A special embodiment of the present invention is described by the class of compounds of Formula V wherein:

$R_2$ is hydrogen, alkyl, aryl or aralkyl; and $R_3$ is hydrogen, alkyl or part of a double bond.

Representative compounds of the present invention include:

12α-(2,2-dimethyl)butyryloxy-3α-hydroxy-17a-[E-2-(4(R)-hydroxy-3,4,5,6-tetrahydro-2H-pyran-2-on-6(S)-yl)ethenyl]-D-homo-5β-androst-17-ene, 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androstane, 7α-acetoxy-12α-(2,2-dimethyl)butyryloxy-3α-hydroxy-17β-[3-(4(R)-hydroxy-3,4,5,6-tetrahydro-2H-pyran-2-on-6(R)-yl)-2-propyl]-5β-androstane, 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androst-8(14)ene, 12α-(2,2-dimethyl)butyryloxy-3α-hydroxy-17β-[2-(4(R)-hydroxy-3,4,5,6-tetrahydro-2H-pyran-2-on-6(R)-yl)-ethyl]-5β-androst-8(14)-ene, 12α-(2,2-dimethyl)butyryloxy-3α-hydroxy-17a-[E-2-(4(R)-hydroxy-3,4,5,6-tetrahydro-2H-pyran-2-on-6(S)-yl)ethenyl]-D-homo-5α-androst-17-ene, 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5α-androstane, 7α-acetoxy-12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5α-androstane, 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5α-androst-8(14)ene, 12α-(2,2-dimethyl)butyryloxy-3α-hydroxy-17β-[2-(4(R)-hydroxy-3,4,5,6-tetrahydro-2H-pyran-2-on-6(R)-yl)-ethyl]-5α-androst-8(14)-ene, 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]androst-1,3,5(10)-triene, 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]androst-1,3,5(10),8(14)tetraene, 7α-acetoxy-12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]androst-1,3,5(10)-triene, 12α-(2,2-dimethyl)butyryloxy-3α-hydroxy-17a-[E-2-(4(R)-hydroxy-3,4,5,6-tetrahydro-2H-pyran-2-on-6(S)-yl)ethenyl]-D-homoandrost-5(6),17-diene, and 12α-(2,2-dimethyl)butyryloxy-3α-hydroxy-17β-[2-(4(R)-hydroxy-3,4,5,6-tetrahydro-2H-pyran-2-on-6(R)-yl)-ethyl]androst-5(6)-ene.

The compounds of the present invention contain asymmetric centers on the steroid ring, at the 4 and 6 positions of the 4-hydroxy-3,4,5,6-tetrahydro-2H-pyran-2-one ring and at the corresponding positions of the ring-opened hydroxy acid form. These asymmetric centers may independently be in either the R or S configuration. The present invention comprises the individual stereoisomers and mixtures thereof.

The compounds of the present invention may be useful in the form of the free base or acid or in the form of a pharmaceutically acceptable salt thereof. Furthermore, the compounds may be in the lactone or ring-opened hydroxy acid form. All forms are within the scope of the invention.

Where the steroidyl moiety is substituted with a basic moiety, acid addition salts may be formed and are simply a more convenient form for use; and in practice, use of the salt form inherently amounts to use of the free base form of the lactone or ring-opened hydroxy acid. The acids which can be used to prepare the acid addition salts include preferably those which produce, when combined with the free base, pharmaceutically acceptable salts, that is, salts whose anions are non-toxic to the animal organism in pharmaceutical doses of the salts, so that the beneficial hypocholesterolemic properties inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as for example, when the salt is formed only for purposes of purification, and indentification, or when it is used as intermediate in preparing a pharmaceutically acceptable salt by ion exchange procedures. Pharmaceutically acceptable salts within the scope of the invention are those derived from the following acids: mineral acids such as hydrochloric acid, sulfuric acid, phosphoric acid and sulfamic acid; and organic acids such as acetic acid, citric acid, lactic acid, tartaric acid, malonic acid, methanesufonic acid, ethanesulfonic acid, benzenesulfonic acid, p-toluenesulfonic acid, cyclohexylsulfamic acid, quinic acid, and the like. The corresponding acid addition salts comprise the following: hydrochloride, sulfate, phosphate, sulfamate, acetate, citrate, lactate, tartarate, malonate, methanesulfonate, ethanesulfonate, benzenesulfonate, p-toluenesulfonate, cyclohexylsulfamate and quinate, respectively.

The acid addition salts of the compounds of this invention are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Where the compound of the invention is in the ring-opened hydroxy acid form, base addition salts may be formed and are simply a more convenient form for use; and in practice, use of the salt form inherently amounts to use of the free acid form of the ring-opened hydroxy acid. The bases which can be used to prepare the base addition salts include preferably those which produce, when combined with the free acid, pharmaceutically acceptable salts, that is, salts whose cations are non-toxic to the animal organism in pharmaceutical doses of the salts, so that the beneficial hypocholesterolemic properties inherent in the free acid are not vitiated by side effects ascribable to the cations. Pharmaceutically acceptable salts within the scope of the invention are those derived from the following bases: sodium hydroxide, potassium hydroxide, calcium hydroxide, aluminum hydroxide, lithium hydroxide, magnesium hydroxide, zinc hydroxide, ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, and the like.

Metal salts of compounds of the present invention may be obtained by contacting a hydroxide, carbonate or similar reactive compound of the chosen metal in an aqueous solvent with the ring-opened hydroxy acid. The aqueous solvent employed may be water or it may be a mixture of water with an organic solvent, preferably an alcohol such as methanol or ethanol, a ketone such as acetone, an aliphatic ether such as tetrahydrofuran, or an ester such as ethyl acetate. Such reactions are normally conducted at ambient temperature but they may, if desired, be conducted with heating.

Amine salts of compounds of the present invention may be obtained by contacting an amine in an aqueous solvent with the ring-opened hydroxy acid. Suitable aqueous solvents include water and mixtures of water with alcohols such as methanol or ethanol, ethers such as tetrahydrofuran, nitriles such as acetonitrile, or ketones such as acetone. Amino acid salts may be similarly prepared.

The lactone form of compounds of the present invention may be obtained by lactonizing the ring-opened hydroxy acid form of the compound by ordinary methods known to one skilled in the art. The ring-opened hydroxy acid form of the compound may be obtained by hydrolysis of the lactone form by methods known in the art.

Compounds of this invention may be prepared in accordance with the reaction sequences described below, or can be prepared by methods known in the art. The starting materials used in the preparation of compounds of this invention are known or are commercially available, or can be prepared by known methods or by specific reaction schemes described herein.

The compounds of the present invention, generally, are available by elaborating a preexisting side chain on a steroid starting material to the desired hydroxy acid or lactone, or by introducing the appropriate side chain onto a steroid starting material from which side chain the hydroxy acid and lactone may be prepared.

If it is necessary or desirable to prevent cross-reaction between chemically active substituents, either on the steroid ring system or the side chain, the substituents may be protected by standard blocking groups which may subsequently be removed by known methods to afford the desired product (see, for example, Greene, "Protective Groups in Organic Synthesis," Wiley, N.Y. 1981). Selective protection or deprotection may also be necessary or desirable to allow conversion, addition, or removal of existing substituents to afford the final desired product.

A method for elaborating an existing side chain to the desired ring-opened hydroxy acid and 4-hydroxy-3,4,5,6-tetrahydro-2H-pyran-2-one, along with examples of substituent conversion, protection, and deprotection are shown in Scheme I below.

Scheme I

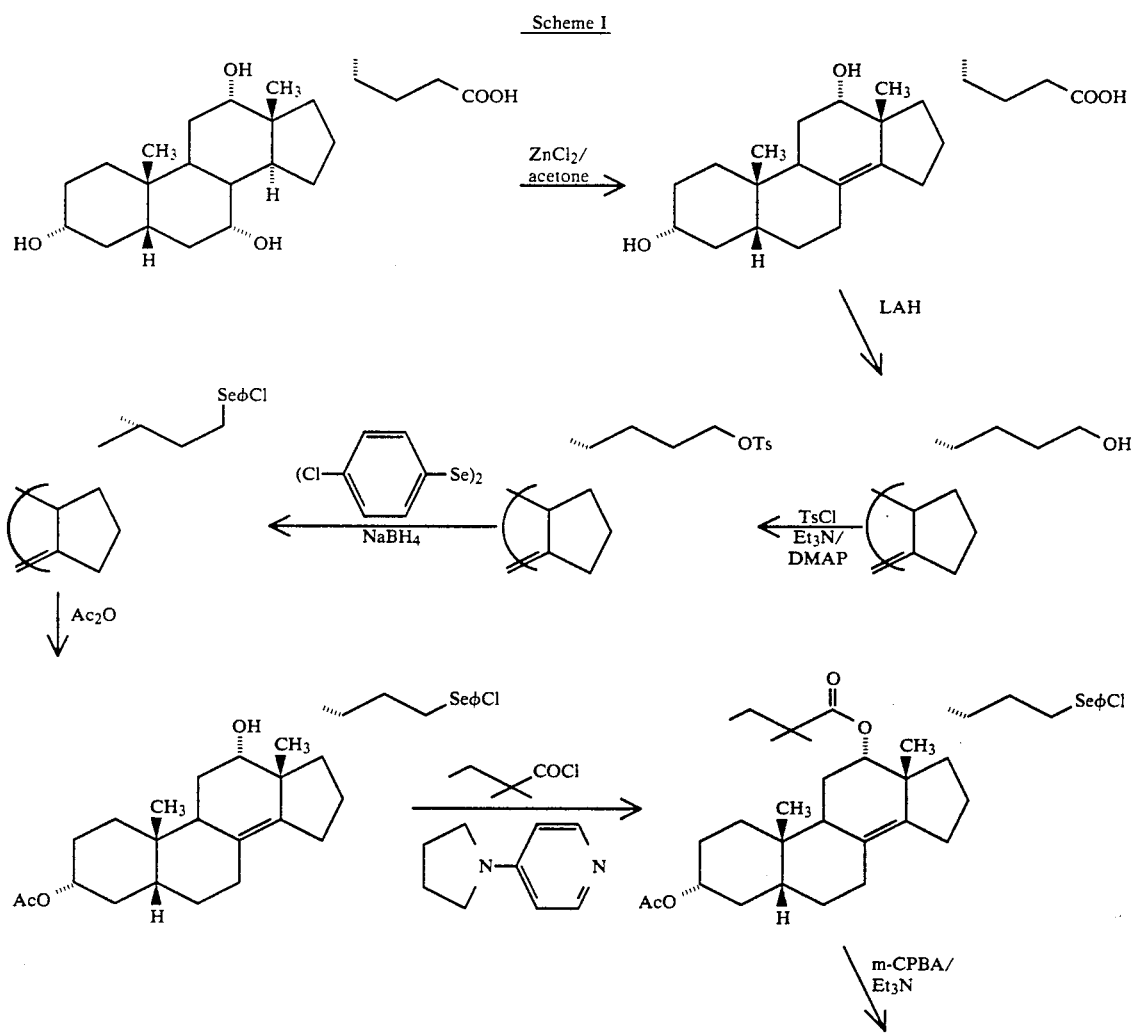

-continued
Scheme I

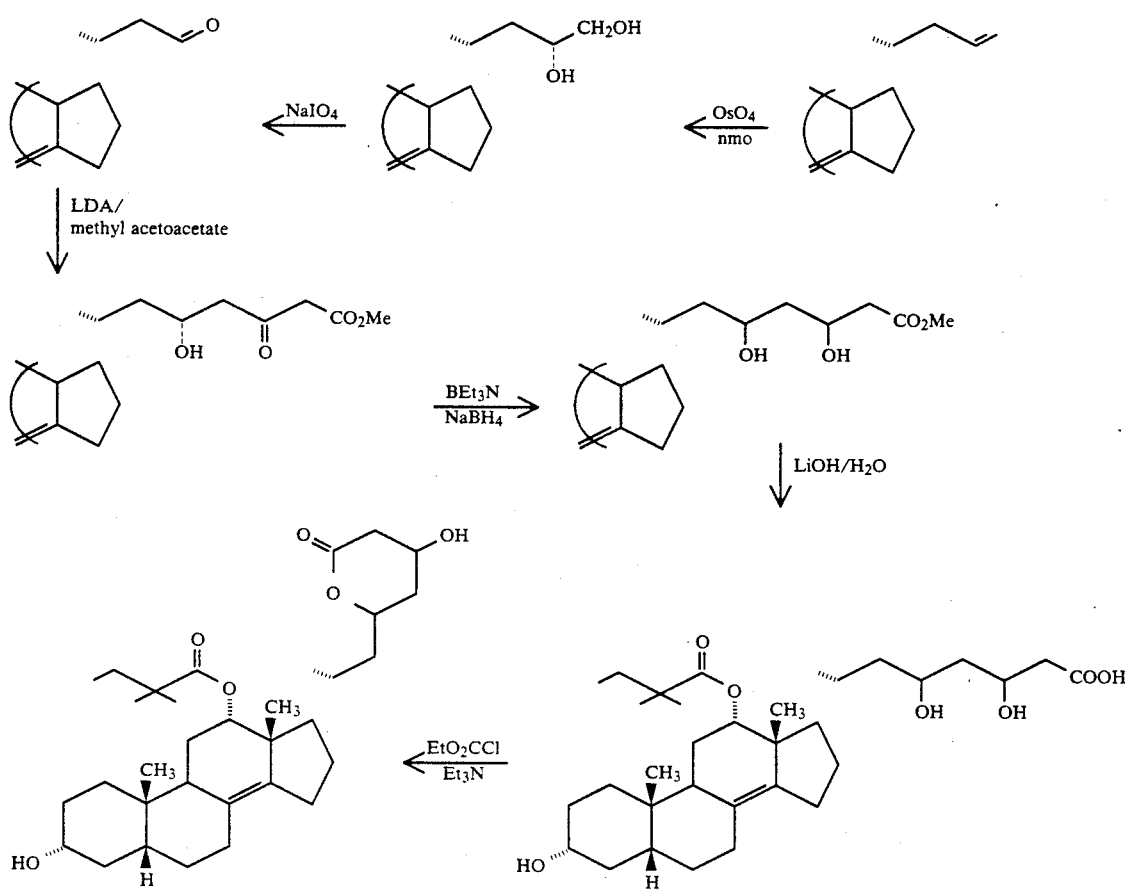

represents the steroidyl group unchanged from the previous step.

Cholic acid is treated with zinc chloride to afford the corresponding chol-8(14)en-24-oic acid which is subsequently reduced by treatment with lithium aluminum hydride to the corresponding alcohol. Treatment of the alcohol with p-toluenesulfonyl chloride in the presence of 4-dimethylaminopyridine and triethylamine gives the tosylate which is then converted to the 4-chlorophenylseleno derivative by treatment with bis(4-chlorophenyl)diselenide in the presence of sodium borohydride.

The 3-hydroxy group on the steroid ring is protected as the acetoxy derivative by treatment with acetic anhydride followed by conversion of the 12-hydroxy to the desired (2,2-dimethyl)butyryloxy derivative by treatment with the appropriate acid chloride in the presence of 4-pyrrolidinopyridine.

Elaboration of the side chain is continued by formation of the olefin by treatment with m-chloroperbenzoic acid to form the corresponding selenoxide followed by thermal elimination in the presence of triethylamine. The corresponding diol is prepared from the olefin by treatment with osmium tetroxide in the presence of 4-methylmorpholine-N-oxide hydrate and the aldehyde is prepared by sodium periodate cleavage of the diol. Treatment of the aldehyde with methyl acetoacetate in the presence of lithium diisopropyl amide affords the methyl-5-hydroxy-3-oxooctanoate which is reduced to the 3,5-dihydroxy compound by treatment with sodium borohydride and triethylborane. Hydrolysis of the ester in the presence of lithium hydroxide affords the desired 3,5-dihydroxyoctanoic acid derivative which can be lactonized, if desired, to the 4-hydroxy-3,4,5,6-tetrahydro-2H-pyran-2-one in the presence of ethyl chloroformate and triethylamine.

An alternative method for elaborating an existing side chain to the desired hydroxy acid or lactone is shown in Scheme II below.

Scheme II

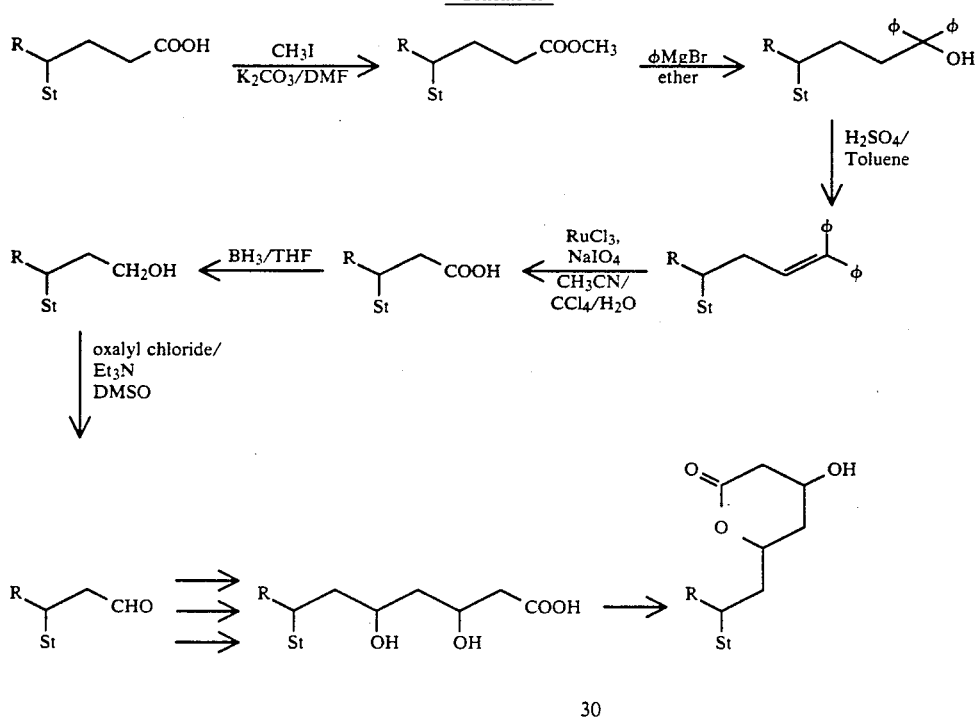

R is hydrogen or lower alkyl and St represents the desired steroidyl group or a protected derivative or precursor thereto.

The carboxylic acid is converted to the methyl ester by treatment with methyl iodide in the presence of potassium carbonate in dimethylformamide. The ester is treated with phenylmagnesium bromide in ether to give the hydroxy diphenyl derivative. Elimination by treatment with sulfuric in toluene yields the diphenyl olefin derivative.

Oxidative cleavage of the olefin with sodium periodate in the presence of ruthenium chloride in acetonitrile, carbon tetrachloride and water gives the corresponding carboxylic acid. The alcohol is prepared from the carboxylic acid by reduction with borane in tetrahydrofuran and the aldehyde is prepared by oxidation of the alcohol. The aldehyde is then converted to the desired lactone or ring-opened hydroxy acid as shown in Scheme I and described above.

As noted above, compounds of the present invention have asymmetric carbon atoms which may, individually, be in either the R or S configuration. As a result, the compounds may be obtained as individual enantiomers, racemic mixtures, or, when two or more asymmetric carbon atoms are present, as a mixture of diastereomers. The product may be synthesized as a mixture of isomers and then the desired isomer separated by conventional techniques such as chromatography or fractional crystallization in the case where diastereomers are to be separated, or by chiral chromatography or separation of diasteromeric salts or derivatives of the isomers by fractional crystallization or chromatography in the case of enantiomers, followed by resolution of the desired product by conventional techniques. Alternatively, synthesis of the compounds may be carried out by known stereospecific processes, or by using the appropriate form of intermediates which would result in obtaining the desired stereoisomer.

The preparations shown in Schemes I and II and described above afford the 4-hydroxy-3,4,5,6-tetrahydro2H-pyran-2-one as a mixture of the 4(R)6(R) and 4(S)6(R) isomers as well as the corresponding mixture of ring-opened hydroxy acids. If it is desired to elaborate an existing side chain to the 4-hydroxy-3,4,5,6-tetrahydro-2H-pyran-2-one or the corresponding ring-opened hydroxy acid in a stereospecific manner, the procedure shown in Scheme III below, for example, is used.

Scheme III

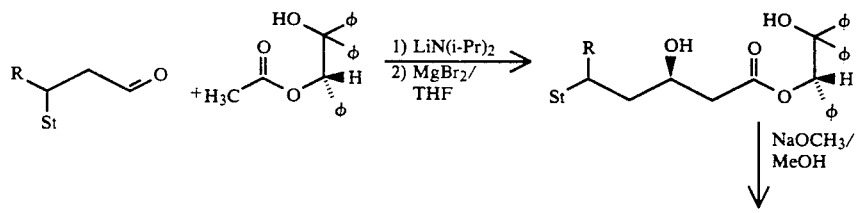

Scheme III

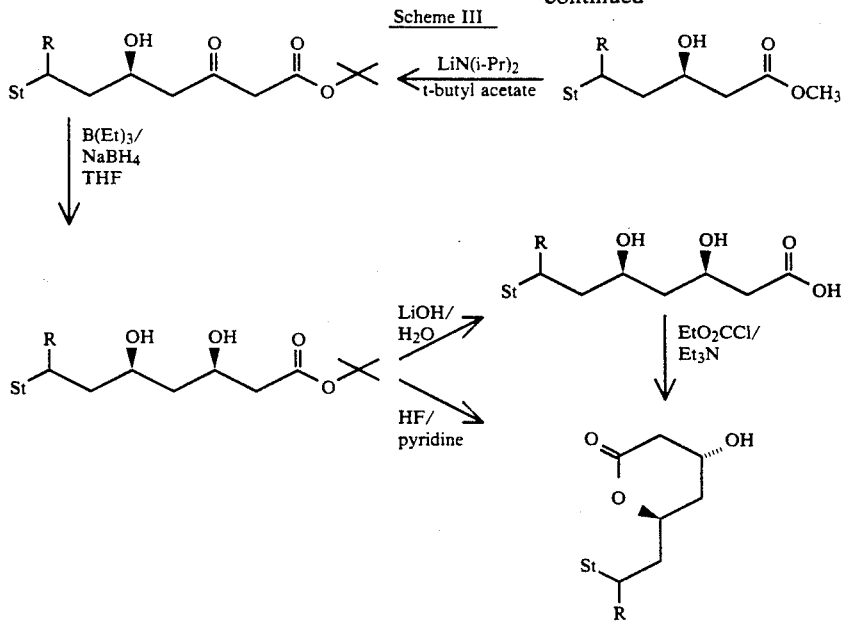

The chiral 3-hydroxy ester intermediate is prepared according to the method of Braun, et al., *Tetrahedron Letters*, 25 (44), 5031 (1984), whereby the appropriate aldehyde is treated with, for example, (S)-2-acetoxy-1,1,2-triphenylethanol in the presence of lithium diisopropyl amide followed by treatment with magnesium bromide. The methyl ester is then prepared by treatment with sodium methoxide in methanol.

Treatment of the methyl ester with tert-butyl acetate in the presence of lithium diisopropylamide in tetrahydrofuran gives the 3-oxo-5-hydroxy t-butyl ester. The 3,5-dihydroxy intermediate is prepared by reduction of the oxo compound with triethyl borane and sodium borohydride in tetrahydrofuran. Alkaline hydrolysis of the dihydroxy compound as described above affords the ring-opened hydroxy acid in the 3(R)5(R) configuration shown in Scheme III, from which the 4(R)6(R)-4-hydroxy-3,4,5,6-tetrahydro-2H-pyran-2-one is available by the procedure described above. Alternatively, the lactone may be prepared directly by treatment of the ester with hydrogen fluoride/pyridine.

In a similar manner the 4(S)6(S) lactones and 3(S)5(S) hydroxy acids are prepared using (R)-2-acetoxy-1,1,2-triphenylethanol in the initial step.

Compounds of the present invention are also prepared by coupling appropriate side chain precursors to an existing steroidyl group by known methods. An example preparation of a side chain precursor is shown in Scheme IV below.

Scheme IV

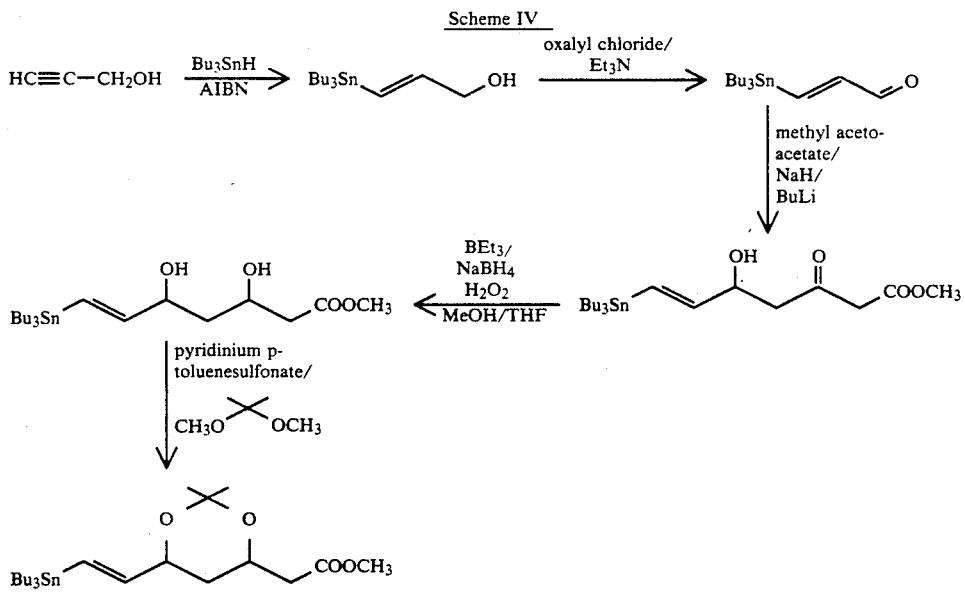

Propargyl alcohol is treated with tributyltin hydride in the presence of $\alpha,\alpha'$-azoisobutyronitrile to give the tributylstannylpropenol which is converted to the acrolein by treatment with oxalyl chloride, dimethylsulfoxide and triethylamine in methylene chloride. The 3-oxo- 5-hydroxyheptenoic acid ester is prepared by treatment of the acrolein with methylacetoacetate, sodium hydride and butyllithium.

The oxo derivative is reduced to the dihydroxy compound by treatment with triethylborane and sodium borohydride, followed by treatment with aqueous hydrogen peroxide. Protection of the hydroxy groups is accomplished, for example, with 2,2-dimethoxypropane in the presence of pyridinium p-toluene sulfonate to give the desired precursor.

The preparation shown in Scheme IV and described above gives the intermediate 3,5-dihydroxyheptenoate ester derivative as a mixture of the 3(R)5(S) and 3(S)5(R) isomers and the protected precursor as the corresponding mixture. If it is desired to prepare an analogous precursor in a stereospecific manner, the preparation shown in Scheme V below is used.

The tributylstannylacrolein is treated with the magnesium enolate derived from (S)-2-acetoxy-1,1,2-triphenylethanol to give the chiral hydroxy intermediate which is treated with sodium methoxide in methanol to give the corresponding methyl ester. Claisen condensation of this ester with tert-butyl acetate affords the t-butyl tributylstannyl-5(S)-hydroxy-3-oxoheptenenoate which is converted to the 3(R)5(S)-dihydroxy heptenoate ester by reduction as described above and subsequently to the protected chiral precursor as shown in Scheme IV and described above. If it is desired to prepare the enantiomeric intermediate dihydroxy compound, i.e., the 3(S)5(R) isomer, the starting acrolein is treated initially with (R)-2-acetoxy-1,1,2-triphenylethanol.

The precursor is then coupled to a steroidyl group with an available keto group and compounds of the

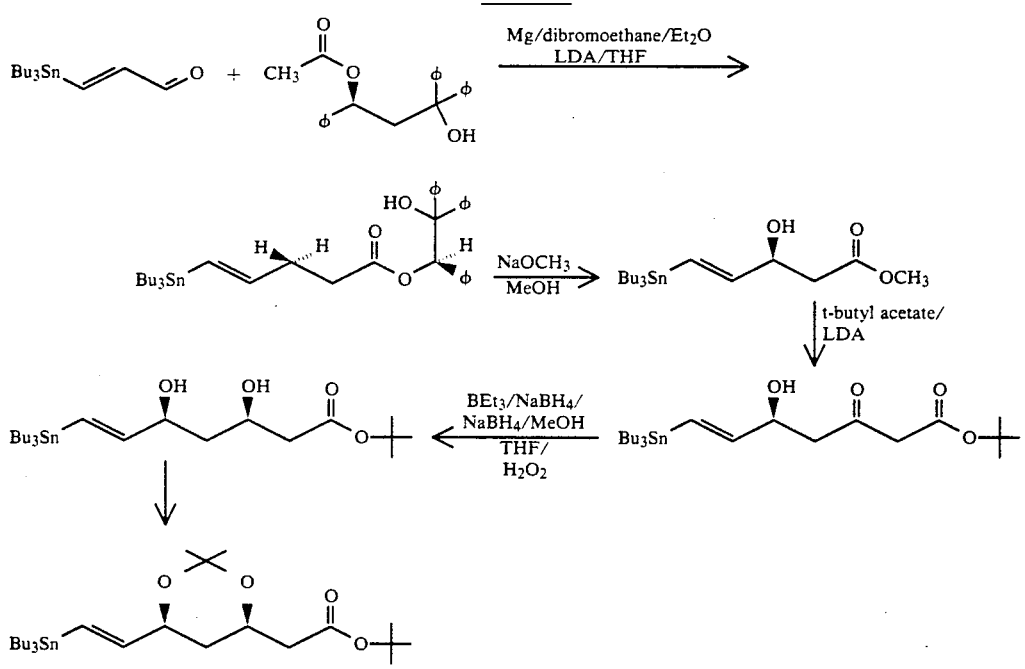

present invention prepared, as shown in Scheme VI below using the chiral precursor as an example.

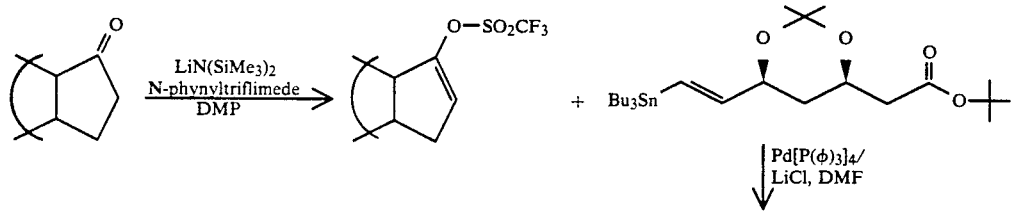

-continued
Scheme VI

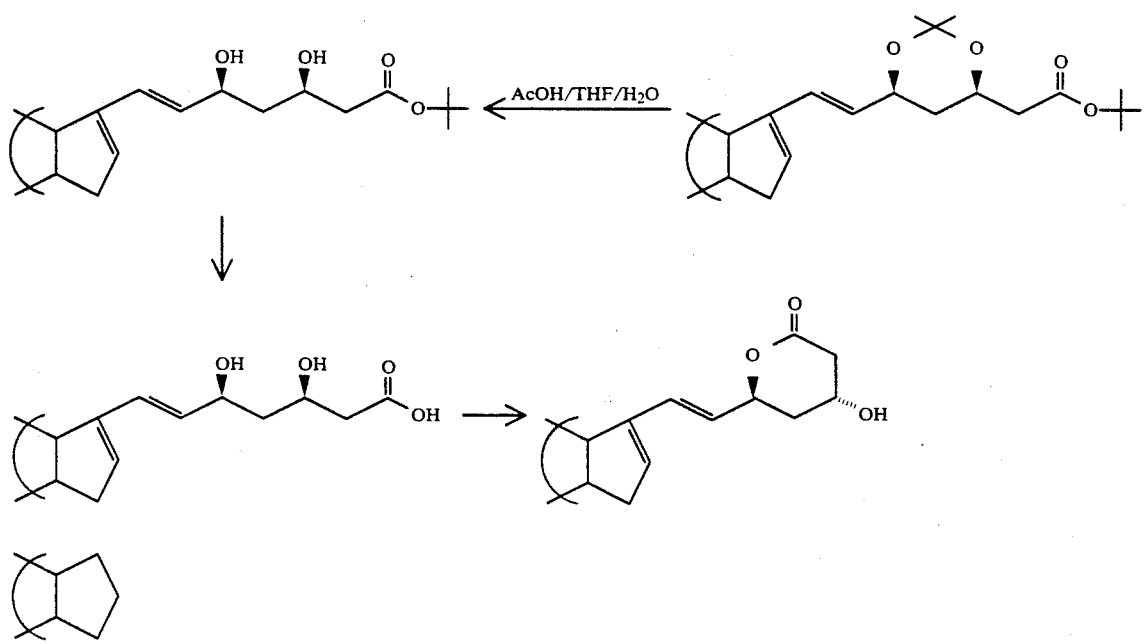

represents the D ring of an appropriately protected steroidyl group or an appropriate precursor thereto.

The keto steroid is converted to the enol triflate by treatment with N-phenyltriflimide in the presence of lithium bis(trimethylsilyl)amide and 1,3-dimethyl-3,4,5,6-tetrahydro-2(1H)-pyrimidinone. The triflate is then treated with the tributylstannyl precursor in the presence of tetrakis(triphenylphosphine)palladium and lithium chloride in dimethylformamide to give the coupled product. Deprotection with acetic acid and water in tetrahydrofuran affords the 3,5-dihydroxy ester which is hydrolyzed to the desired ring-opened hydroxy acid from which is prepared the 4-hydroxy-3,4,5,6-tetrahydro-2H-pyran-2-one, if desired, as shown in Scheme I and described above. When the chiral precursor derived from (S)-2-acetoxy-1,1,2-triphenylethanol is used in this preparation, the 4(R)-hydroxy-6(S)-steroidylethenyl 3,4,5,6-tetrahydro-2H-pyran-2-one, and the corresponding hydroxy acid, are prepared. A mixture of the 4(R)6(S) and 4(S)6(R) isomers is available by using the achiral precursor shown in Scheme IV and described above, or the 4(S)6(R) isomer is prepared, if desired, by using the precursor derived from (R)-2-acetoxy-1,1,2-triphenylethanol.

The present invention is further explained by the following illustrative examples.

The nomenclature used for the steroid derivatives in the following examples is based upon that shown for the steroids in the figure below:

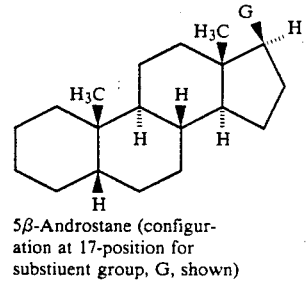

5β-Androstane (configuration at 17-position for substiuent group, G, shown)

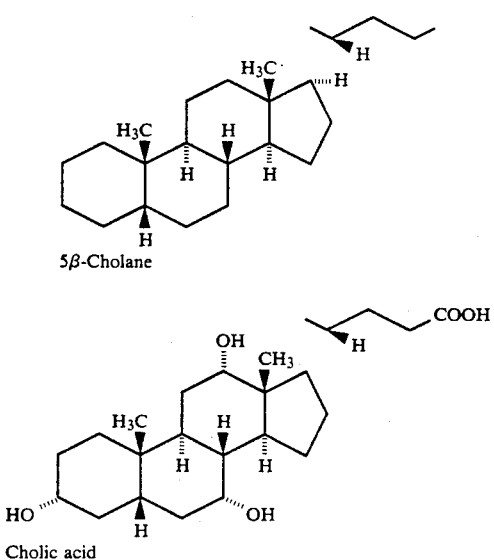

5β-Cholane

Cholic acid

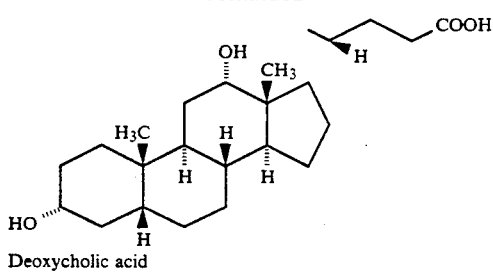

Deoxycholic acid

EXAMPLE 1A

Preparation of 2,2-dimethyl-4-methoxycarbonylmethyl-6-[E-2-(tributylstannyl)ethenyl]-1,3-dioxane Step 1: Preparation of E-3-tributylstannyl-2-propen-1-ol To a mixture of propargyl alcohol (2.24 g) and α,α'-azoisobutyronitrile (0.10 g) in anhydrous toluene (150 ml) is added tributyltin hydride (12.9 ml) and the mixture heated at reflux for about 2.5 hours, cooled and concentrated in vacuo. The crude product is purified by flash chromatography in 15% ether in hexane to give the desired product.

Step 2: Preparation of E-3-tributylstannylacrolein

A solution of oxalyl chloride (17.3 ml) in anhydrous methylene chloride (62 ml) is cooled to −78° C. and dimethylsulfoxide (3.7 ml) is added dropwise. The mixture is stirred for 15 minutes, E-3-tributylstannyl-2-propen-1-ol (10.7 g) in methylene chloride (26 ml) added dropwise, stirred for about 10 minutes, and triethylamine (19.4 ml) added. Stirring is stopped, the mixture allowed to warm to room temperature, then stirred for about 5 minutes, diluted with ether, and washed with water. The organic solution is dried over magnesium sulfate, filtered and concentrated in vacuo. The crude product is purified by flash chromatography to give the desired product.

Step 3: Preparation of E-methyl-5-hydroxy-3-oxo-7-tributylstannyl-6-heptenoate

A suspension of sodium hydride (1.28 g) in tetrahydrofuran (70 ml) is cooled to 0° C. and methyl acetoacetate (3.2 ml) added over about 1 minute. The mixture is stirred for about 15 minutes at 0° C., 2.5M n-butyllithium in hexane (12.3 ml) added, stirred for about 20 minutes, E-3-tributylstannylacrolein (10.0 g) in tetrahydrofuran (25 ml) added over five minutes and stirred for about 15 minutes. The mixture is quenched by slow addition of 1M hydrochloric acid, diluted with ether. The aqueous layer is back-extracted with ether and the combined organic solutions washed with saturated sodium chloride solution, dried over magnesium sulfate, filtered, and concentrated in vacuo. The crude product is purified by flash chromatography in 25% ethyl acetate in hexane to give the desired product.

Step 4: Preparation of E-methyl 3,5-dihydroxy-7-tributylstannyl-6-heptenoate

A mixture of E-methyl-5-hydroxy-3-oxo-7-tributylstannyl-6-heptenoate (7.19 g) and 1M triethylborane in tetrahydrofuran (23.4 ml) in anhydrous tetrahydrofuran (40 ml) is stirred at 20°–25° C. for about 20 minutes. The mixture is cooled to −78° C., sodium borohydride (0.677 g) added, stirred for 10 minutes, methanol (15 ml) added over about 30 minutes maintaining temperature below −68° C. and stirred at −78° C. for about 2 hours. The mixture is allowed to warm to −60° C. and 30% hydrogen peroxide (35 ml) in water (86 ml) is added. The mixture is allowed to warm to room temperature while stirring for about 30 minutes, diluted with ether and the layers separated. The organic solution is washed with saturated sodium chloride solution, dried over magnesium sulfate, filtered and concentrated in vacuo. The crude product is purified by flash chromatography in 25% ethyl acetate in hexane to give the desired product.

Step 5: Preparation of 2,2-dimethyl-4-methoxycarbonylmethyl-6-[E-2-(tributylstannyl)ethenyl]-1,3-dioxane A mixture of E-methyl 3,5-dihydroxy-7-tributylstannyl-6-heptenoate (4.18 g), 2,2-dimethoxypropane (18 ml) and pyridinium p-toluene sulfonate (0.227 g) is stirred in anhydrous methylene chloride (4.5 ml) at room temperature for about 20 hours, diluted with ether, washed with saturated sodium bicarbonate solution then saturated sodium chloride solution. The organic solution is dried over magnesium sulfate, filtered and concentrated in vacuo. The crude product is purified by flash chromatography in 10% ether in hexane to give the desired product.

EXAMPLE 1

Preparation of 12α-(2,2-dimethyl)butyryloxy-3α-hydroxy-17a-[E-2-(4(R)-hydroxy-3,4,5,6-tetrahydro-2H-pyran-2-on-6(S)-yl)ethenyl]-D-homo-5β-androst-17-ene and 12α-(2,2-dimethyl)butyryloxy-3α-hydroxy-17a-[E-2-(4(S)-hydroxy-3,4,5,6-tetrahydro-2H-pyran-2-on-6(R)-yl)ethenyl]-D-homo-5β-androst-17-ene Step 1: Preparation of methyl deoxycholate To a mixture of deoxycholic acid (25.0 g) and anhydrous potassium carbonate (8.8 g) in anhydrous dimethylformamide (65 ml) is added methyl iodide (4.8 ml) and the mixture stirred at room temperature for about 4 hours. The mixture is diluted with ethyl acetate and washed four times with water and once with saturated sodium chloride solution. The organic solution is dried over magnesium sulfate, filtered, and concentrated in vacuo. The crude product is purified by flash chromatography in 80% ethyl acetate in hexane to give the desired product.

Step 2: Preparation of 3α,12α-dihydroxy-17β-[(1,1-diphenyl)-1-pentanol-4-yl]-5β-androstane A solution of methyl deoxycholate (36.6 g) in anhydrous tetrahydrofuran (180 ml) is added to a solution of 3.0M phenylmagnesium bromide in ether (270 ml) in tetrahydrofuran (90 ml) at such a rate so as to maintain a gentle reflux. The mixture is stirred for about 2 hours, quenched by slow addition of saturated aqueous ammonium chloride solution and diluted with ether. The organic solution is washed with saturated ammonium chloride solution, saturated sodium chloride solution, dried over magnesium sulfate, filtered, and concentrated in vacuo to give the desired product which is used, without further treatment, for the next step.

Step 3: Preparation of 3α, 12α-dihydroxy-17β-[(1,1-diphenyl)-1-penten-4-yl]-5β-androstane A mixture of the crude 3α, 12α-dihydroxy-17β-[(1,1-diphenyl)-1-pentanol-4-yl]-5β-androstane (25.4 g) and concentrated sulfuric acid (2.6 ml) in dry toluene (450 ml) is stirred at 50° C. for about 30 minutes, cooled, and washed with water until the wash is pH neutral. The organic solution is dried over magnesium sulfate, filtered, and concentrated in vacuo. The crude product is purified by flash chromatography in 35% ethyl acetate in hexane to give the desired product.

Step 4: Preparation of 3α, 12α-diacetoxy-17β-[(1,1-diphenyl)-1-penten-4-yl]-5β-androstane A mixture of 3α, 12α-dihydroxy-17β-[(1,1-diphenyl)-1-penten-4-yl]-5β-androstane (15.6 g), pyridine (14.8 ml), acetic anhydride (57.4 ml), 4-dimethylaminopyridine (3.71 g) and toluene (60 ml) is stirred at room temperature for about 30 minutes, diluted with ether and water and the layers are separated. The organic solution is washed water, dried over magnesium sulfate, filtered and concentrated in vacuo. The crude product is crystallized from 25% ether in hexane to give the desired product as an off-white solid.

Step 5: Preparation of 3α, 12α-diacetoxy-17β-[(1,1-diphenyl)-1,4-pentadien-4-yl]-5β-androstane A mixture of 3α, 12α-diacetoxy-17β-[(1,1-diphenyl)-1-penten-4-yl]-5β-androstane (7.24 g), N-bromosuccinimide (2.26 g) and benzoyl peroxide (0.256 g) in anhydrous carbon tetrachloride (250 ml) is stirred at reflux, while being illuminated with a 275-watt sun lamp, for about 45 minutes. The mixture is cooled, filtered, and concentrated in vacuo. The resulting oil is dissolved in anhydrous pyridine (12.2 ml), the solution refluxed for about 1 hour, and concentrated in vacuo. The residue is dissolved in ether, filtered, and the ether solution washed with dilute sodium chloride solution, dried over magnesium sulfate, filtered and concentrated in vacuo. The crude product is used, without further treatment, for the next step.

Step 6: Preparation of 17β-acetyl-3α, 12α-diacetoxy-5β-androstane

To a solution of the crude 3α, 12α-diacetoxy-17β-[(1,1-diphenyl)-1,4-pentadien-4-yl]-5β-androstane (43.6 g) in carbon tetrachloride (110 ml), acetonitrile (110 ml) and water (146 ml) is added sodium periodate (46.8 g) and ruthenium(III) chloride hydrate (0.373 g). The mixture is stirred vigorously at room temperature for about 1 hour, sodium periodate (5.0 g) and ruthenium-(III) chloride hydrate (0.10 g) are added and stirring continued for about 30 minutes. The mixture is diluted with methylene chloride, washed with water, dried over magnesium sulfate, filtered and concentrated in vacuo. The crude product is purified by flash chromatography in 5% ether in methylene chloride and further purified by flash chromatography in 25% ethyl acetate in hexane to give the desired product.

Step 7: Preparation of 17β-[(1-acetoxy)ethylidene]-3α, 12α-diacetoxy-5β-androstane A mixture of 17β-acetyl-3α, 12α-diacetoxy-5β-androstane (6.26 g) and p-toluenesulfonic acid monohydrate (2.51 g) in acetic anhydride (250 ml) is heated to reflux and solvent is allowed to distil from the mixture for about 9 hours, during which time 500 ml of acetic anhydride is added to replace that lost by distillation. The mixture is allowed to cool, diluted with water and ether, the layers separated and the organic layer washed with water and saturated sodium bicarbonate solution, dried over magnesium sulfate, filtered and concentrated in vacuo to give the desired product which was used, without further treatment, for the next step.

Step 8: Preparation of 3α, 12α-diacetoxy-5β-androstan-17-one

A mixture of 17β-[(1-acetoxy)ethylidene]-3α, 12α-diacetoxy-5β-androstane (12.9 g), sodium periodate (17.8 g) and ruthenium(III) chloride hydrate (0.288 g) in acetonitrile (42 ml), carbon tetrachloride (42 ml) and water (65 ml) is stirred vigorously for about 30 minutes, diluted with ether and washed with water and brine. The organic solution is dried over magnesium sulfate, filtered and concentrated in vacuo. The residue is dissolved in ether and filtered through silica gel and the filtrate concentrated in vacuo to give the desired product mixed with 17-acetyl-3α, 12α-diacetoxy-17-hydroxy-5β-androstane.

This mixture (11.8 g) is dissolved in acetic acid (110 ml) and water (40 ml), sodium periodate (12 g) is added and the mixture stirred at 65° C. for about 16 hours. Sodium periodate (12 g) is added to the mixture and stirring continued at 65° C. for about 4 hours. The mixture is cooled, diluted with ethyl acetate, washed with water and the organic solution dried over magnesium sulfate, filtered and concentrated in vacuo. The crude product is purified by flash chromatography in 25% ethyl acetate in hexane to give the desired product.

Step 9: Preparation of 3α, 12α-dihydroxy-5β-androstan-17-one

A mixture of 3α, 12α-diacetoxy-5β-androstan-17-one (5.5 g) and lithium hydroxide monohydrate (1.7 g) in a solution of methanol (20 ml), tetrahydrofuran (20 ml) and water (20 ml) is stirred at room temperature for about two hours, diluted with ethyl acetate and washed three times with water. The organic solution is dried over magnesium sulfate, filtered and concentrated in vacuo. Benzene is azeotroped from the residue to give the desired product which is used, without further treatment, for the next step.

Step 10: Preparation of 3α-tert-butyldimethylsilyloxy-12α-hydroxy-5β-androstan-17-one A mixture of 3α, 12α-dihydroxy-5β-androstan-17-one (4.29 g), tert-butyldimethylsilyl chloride (3.26 g), 4-dimethylaminopyridine (0.17 g) and imidazole (1.9 g) in dimethylformamide (38 ml) is stirred at room temperature for about 1 hour, diluted with ether and washed with water. The organic solution is dried over magnesium sulfate, filtered and concentrated in vacuo to give the desired product which is used, without further treatment, for the next step.

Step 11: Preparation of 12α-(2,2-dimethyl)butyryloxy-3α-tert-butyldimethylsilyloxy-5β-androstan-17-one 3α-tert-butyldimethylsilyloxy-12α-hydroxy-5β-androstan-17-one (5.9 g), 4-pyrrolidinopyridine (0.30 g) and 2,2-dimethylbutyryl chloride (6 ml) are dissolved in pyridine (30 ml) and the solution warmed to 85° C., stirred at that temperature for about 3 hours, cooled, diluted with ether and washed with water, then 0.5M hydrochloric acid. The organic solution is dried over magnesium sulfate, filtered and concentrated in vacuo. The crude product is purified by flash chromatography in a gradient of 20% to 30% ether in hexane to give the desired product.

Step 12: Preparation of 12α-(2,2-dimethyl)butyryloxy-3α-tert-butyldimethylsilyloxy-17-trimethylsilyloxy-5β-androst-16-ene A mixture of 1.0M lithium bis(trimethylsilyl)amide in hexanes (3 ml) and tetrahydrofuran (3 ml) is cooled to −78° C. and the 12α-(2,2-dimethyl)butyryloxy-3α-tert-butyldimethylsilyloxy-5β-androstan-17-one (1.15 g) in tetrahydrofuran (1 ml) is added dropwise. The mixture is stirred for about 10 minutes and chlorotrimethylsilane (0.38 ml) added. The resulting solution is warmed to room temperature, diluted with hexane and washed with water. The organic solution is dried over magnesium sulfate, filtered, evaporated in vacuo to give the desired product which is used, without further treatment, for the next step.

Step 13: Preparation of 12α-(2,2-dimethyl)butyryloxy-3α-tert-butyldimethylsilyloxy-17β-trimethylsilyloxy-16α, 17-dihydro-3'H-cycloprop[16,17]-5β-androstane 12α-(2,2-dimethyl)butyryloxy-3α-tert-butyldimethylsilyloxy-17-trimethylsilyloxy-5β-androst-16-ene (0.60 g) is dissolved in ether (3 ml) and the solution cooled to 0° C. 1.0M diethyl zinc in hexane (2 ml) is added, then diiodomethane (0.162 ml) is added dropwise and the mixture stirred for about 15 minutes, warmed to room temperature, stirred at room temperature for about 4 hours, refluxed for about 17 hours, cooled, diluted with ether and washed with water. The organic solution is dried over magnesium sulfate, filtered, and concentrated in vacuo to give the desired product which is used, without further treatment, for the next step.

Step 14: Preparation of 12α-(2,2-dimethyl)butyryloxy-3α-tert-butyldimethylsilyloxy-D-homo-5β-androst-16-en-17a-one All of the 12α-(2,2-dimethyl)butyryloxy-3α-tert-butyldimethylsilyloxy-17β-trimethylsilyloxy-16α, 17-dihydro-3'H-cycloprop[16,17]-5β-androstane from Step 13 is dissolved in dimethylformamide (2 ml) and ferric chloride (0.41 g) is added. The mixture is stirred at room temperature for about 1 hour, at 85° C. for about 1.5 hours, cooled, diluted with ether and washed with water. The organic solution is dried over magnesium sulfate, filtered, and concentrated in vacuo. The crude product is purified by flash chromatography in 30% ether in hexane to give the desired product.

Step 15: Preparation of 12α-(2,2-dimethyl)butyryloxy-3α-tert-butyldimethylsilyloxy-17a-trifluoromethylsulfonyloxy-D-homo-5β-androst-17-ene 12α-(2,2-dimethyl)butyryloxy-3α-tert-butyldimethylsilyloxy-D-homo-5β-androst-16-en-17a-one (0.26 g) is dissolved in tetrahydrofuran (2 ml) and the solution cooled to −78° C. 1.0M lithium tri-sec-butylborohydride in tetrahydrofuran (0.6 ml) is added dropwise, the solution stirred for about 30 minutes, N-phenyltrifluoromethanesulfonimide (0.214 g) in tetrahydrofuran (0.5 ml) and 1,3-dimethyl-3,4,5,6-tetrahydro-2(1H)-pyrimidione (0.5 ml) are added, the mixture allowed to warm to room temperature and stirred for about 16 hours. The mixture is diluted with hexane and washed with water. The organic solution is dried over magnesium sulfate, filtered and concentrated in vacuo. The crude product is purified by flash chromatography in 3% ether in hexane to give the desired product.

Step 16: Preparation of 12α-(2,2-dimethyl)butyryloxy-3α-tert-butyldimethylsilyloxy-17a-[E-2-[(4-methoxycarbonylmethyl-2,2-dimethyl)-1,3-dioxan-6-yl]ethenyl]-D-homo-5β-androst-17-ene A mixture of 12α-(2,2-dimethyl)butyryloxy-3α-tert-butyldimethylsilyloxy-17a-trifluormethylsulfonyloxy-D-homo-5β-androst-17-ene (0.80 g) and 2,2-dimethyl-4-methoxycarbonylmethyl-6-[E-2-(tributylstannyl)ethenyl]-1,3-dioxane (0.604 g) is dried by azeotroping with toluene and the residue dissolved in dimethylformamide (3 ml). Tetrakis(triphenylphosphine)palladium (0.042 g) is added, the solution degassed and added to a solution of lithium chloride (0.264 g) in dimethylformamide (3 ml). The resulting solution is heated at 150° C. for about 2 hours, cooled, diluted with ether and washed with water. The organic solution is dried over magnesium sulfate, filtered and concentrated in vacuo. The crude product is purified by flash chromatography in a gradient of 30-40% ether in hexane to give the desired product.

Step 17: Preparation of 17a-[E-(3,5-dihydroxy-6-methoxycarbonyl)hex-1-enyl]-12α-(2,2-dimethyl)butyryloxy-3α-hydroxy-D-homo-5β-androst-17-ene A mixture 12α-(2,2-dimethyl)butyryloxy-3α-tert-butyldimethylsilyloxy-17a-[E-2-[(4-methoxycarbonylmethyl-2,2-dimethyl)-1,3-dioxan-6-yl]ethenyl]-D-homo-5β-androst-17-ene (0.146 g) and acetic acid (1 ml) is stirred in water (1 ml) at room temperature for about 16 hours. The mixture is diluted with ether and washed with water. The organic solution is dried over magnesium sulfate, filtered and concentrated in vacuo. Toluene is azeotroped from the residue and the crude product purified by flash chromatography in 60% ether in hexane to give the desired product.

Step 18: Preparation of 12α-(2,2-dimethyl)butyryloxy-3α-hydroxy-17a-[E-2-(4(R)-hydroxy-3,4,5,6-tetrahydro-2H-pyran-2-on-6(S)-yl)ethenyl]-D-homo-5β-androst-17-ene and 12α-(2,2-dimethyl)butyryloxy-3α-hydroxy-17a-[E-2-(4(S)-hydroxy-3,4,5,6-tetrahydro-2H-pyran-2-on-6(R)-yl)ethenyl]-D-homo-5β-androst-17-ene 17a-[E-(3,5-dihydroxy-6-methoxycarbonyl)hex-1-enyl]-12α-(2,2-dimethyl)butyryloxy-3α-hydroxy-D-homo-5β-androst-17-ene (0.054 g) is dissolved in a solution of tetrahydrofuran (0.3 ml), methanol (0.2 ml), and water (0.2 ml) and lithium hydroxide monohydrate (0.25 g) added and the mixture stirred for about 40 minutes, acidified with 1M hydrochloric acid and diluted with ethyl acetate. The organic solution is washed with water, brine, dried over magnesium sulfate, filtered, concentrated in vacuo, then azeotroped with toluene. The residue is dissolved in methylene chloride (0.5 ml), triphenylphosphine (0.078 g) and 2,2'-dipyridyl disulfide (0.08 g) are added and the mixture stirred at room temperature for about 15 minutes, diluted with ether, and washed with water. The organic solution is dried over magnesium sulfate, filtered, and concentrated in vacuo. The crude product is purified by flash chromatography in ether, followed by flash chromatography is 80% methylene chloride in ether to give the desired product as a 50:50 mixture of the 4(R)6(R) and 4(S)6(S) isomers.

EXAMPLE 2

Preparation of
12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androstane and
12α-(2,2-dimethyl)butyryloxy-3α-hydroxy-17β-[3-(4(S)-hydroxy-3,4,5,6-tetrahydro-2H-pyran-2-on-6(S)-yl)-2(R)-2-propyl]-5β-androstane

Step 1: Preparation of
3α-tert-butyldiphenylsilyloxy-17β-[(1,1-diphenyl)-1-penten-4-yl]-12α-hydroxy-5β-androstane To a mixture of 3α, 12α-dihydroxy-17β-[(1,1-diphenyl)-1-penten-4-yl]-5β-androstane (10.2 g), imidazole (1.64 g) and 4-dimethylaminopyridine (0.256 g) in dimethylformamide (30 ml) is added tert-butylchlorodiphenylsilane (6.04 g) and the mixture stirred for about 3.5 hours and diluted with ether/hexane (1:1). The solution is washed with saturated sodium bicarbonate, dried over magnesium sulfate, filtered and concentrated in vacuo. The crude product is purified by flash chromatography in 50% ether in hexane to give the desired product.

Step 2: Preparation of
3α-tert-butyldiphenylsilyloxy-12α-(2,2-dimethyl)-butyryloxy-17β-[(1,1-diphenyl)-1-penten-4-yl]-5β-androstane 3α-tert-butyldiphenylsilyloxy-17β-[(1,1-diphenyl)-1-penten-4-yl]-12α-hydroxy-5β-androstane (10.6 g), 4-pyrrolidinopyridine (0.207 g) and 2,2-dimethylbutyryl chloride (2.25 g) are dissolved in pyridine (55 ml) and the solution warmed to 110° C., stirred for about 1 hour, additional 2,2-dimethylbutyryl chloride (2.25 g) is added and stirring continued for about 14 hours at 110° C. The mixture is cooled, diluted with 20% ether in hexane and washed with water, then 1M hydrochloric acid. The organic solution is dried over magnesium sulfate, filtered and concentrated in vacuo. The crude product is purified by flash chromatography in 10% ether in hexane to give the desired product.

Step 3: Preparation of
3(R)-3-[[3α-tert-butyldiphenylsilyloxy-12α-(2,2-dimethyl)butyryloxy]-5β-androstan-17β-yl]butanoic acid A mixture of 3α-tert-butyldiphenylsilyloxy-12α-(2,2-dimethyl)butyryloxy-17β-[(1,1-diphenyl)-1-penten-4-yl]-5β-androstane (0.421 g), sodium periodate (0.350 g) and ruthenium(III) chloride hydrate (0.007 g) in carbon tetrachloride (1.5 ml), acetonitrile (1.5 ml) and water (2.4 ml) is stirred at room temperature for about 45 minutes, diluted with ether and washed with water. The organic solution was dried over magnesium sulfate, filtered, and concentrated in vacuo. The crude product was purified by flash chromatography in 35% ether in petroleum ether to give the desired product.

Step 4: Preparation of
3(R)-3-[[3α-tert-butyldiphenylsilyloxy-12α-(2,2-dimethyl)butyryloxy]-5β-androstan-17β-yl]butanol 3(R)-3-[[3α-tert-butyldiphenylsilyloxy-12α-(2,2-dimethyl)butyryloxy]-5β-androstan-17β-yl]butanoic acid (4.8 g) is dissolved in tetrahydrofuran (30 ml). The solution is cooled to 0° C., 1.0M borane in tetrahydrofuran (10.1 ml) is added dropwise and the solution stirred for about 1.7 hours, diluted with ether, washed with saturated sodium bicarbonate solution. The organic solution is dried over magnesium sulfate, filtered, and concentrated in vacuo to give the crude product which is purified by flash chromatography in 40% ether in petroleum ether to give the desired product.

Step 5: Preparation of
3(R)-3-[[3α-tert-butyldiphenylsilyloxy-12α-(2,2-dimethyl)butyryloxy]-5β-androstan-17β-yl]butanal A solution of oxalyl chloride (0.76 ml) in methylene chloride (20 ml) is cooled to −78° C., dimethylsulfoxide (0.74 ml) is added dropwise and the resulting solution stirred for about 15 minutes. 3(S)-3-[[3α-tert-butyldiphenylsilyloxy-12α-(2,2-dimethyl)butyryloxy]-5β-androstan-17β-yl]butanol (4.06 g) in methylene chloride (5 ml) is added and the solution stirred for about 10 minutes. Triethylamine (3.65 ml) is added and the solution warmed to room temperature, diluted with ether and washed with water. The organic solution is dried over magnesium sulfate, filtered and concentrated in vacuo to give the desired product which is used, without further treatment, for the next step.

Step 6: Preparation of
7(R)-methyl-7-[[3α-tert-butyldiphenylsilyloxy-12α-(2,2-dimethyl)butyryloxy-5β-androstan-17β-yl]-5-hydroxy-3-oxooctanoate A solution of diisopropylamine (2.4 ml) in tetrahydrofuran (35 ml) is cooled to −15° C. and 2.5M n-butyllithium in hexanes (6.1 ml) is added dropwise. The solution is stirred for about 15 minutes, cooled to −78° C., and methyl acetoacetate (0.75 ml) is added. The solution is warmed to 0° C., stirred for about 1.5 hours, and 3(R)-3-[[3α-tert-butyldiphenylsilyloxy-12α-(2,2-dimethyl)butyryloxy]-5β-androstan-17β-yl]butanal (4.1 g) in tetrahydrofuran (25 ml) is added over about 5 minutes. The solution is stirred for about 10 minutes, diluted with ether, washed with 0.1M hydrochloric acid, washed with saturated sodium bicarbonate, dried over magnesium sulfate, filtered and concentrated in vacuo. The crude product is purified by flash chromatography in 50% ether in hexane to give the desired product.

Step 7: Preparation of
7(R)-methyl-7-[[3α-tert-butyldiphenylsilyloxy-12α-(2,2-dimethyl)butyryloxy]-5β-androstan-17β-yl]-3,5-dihydroxyoctanoate A mixture of 7(R)-methyl-7-[[3α-tert-butyldiphenylsilyloxy-12α-(2,2-dimethyl)butyryloxy]-5β-androstan-17β-yl]-5-hydroxy-3-oxooctanoate (1.4 g) and 1.0M triethylborane in tetrahydrofuran (2.5 ml) in tetrahydrofuran (4.5 ml) is stirred for about 5 minutes at room temperature, then cooled to −78° C. To the solution is added sodium borohydride (0.077 g), followed by dropwise addition of methanol (1.7 ml) over about 15 minutes. The solution is stirred at −78° C. for about 45 minutes, warmed to −60° C., and a solution of 30% hydrogen peroxide (3.8 ml) in water (8.2 ml) is added over about 20 minutes. The mixture is allowed to warm to room temperature while stirring for about 45 minutes. The mixture is diluted with ether, washed with saturated ammonium chloride solution, washed with saturated sodium bicarbonate solution, then brine, dried over magnesium sulfate, filtered and concentrated in vacuo. The crude product was purified by HPLC in 25% ethyl acetate in hexane to give the desired product.

Step 8: Preparation of 7(R)-7-[[3α-tert-butyldiphenylsilyloxy-12α-(2,2-dimethyl)butyryloxy]-5β-androstan-17β-yl]-3,5-dihydroxyoctanoic acid A mixture of 7(R)-methyl-7-[[3α-tert-butyldiphenylsilyloxy-12α-(2,2-dimethyl)butyryloxy]-5β-androstan-17β-yl]-3,5-dihydroxyoctanoate (0.40 g) and lithium hydroxide monohydrate (0.082 g) in methanol/tetrahydrofuran/water (3:1:1) (3.5 ml) is stirred at 0° to 10° C. for about 1 hour, diluted with ethyl acetate and acidified with 1.0M hydrochoric acid. The organic solution is washed with brine, dried over magnesium sulfate, filtered, and concentrated in vacuo to give the desired product which is used, without further treatment, for the next step.

Step 9: Preparation of 12α-(2,2-dimethyl)butyryloxy-3α-tert-butyldiphenylsilyloxy-17β-[3-(4(R)-hydroxy-3,4,5,6-tetrahydro-2H-pyran-2-on-6(R)-yl)-2(R)-2-propyl]-5β-androstane and 12α-(2,2-dimethyl)butyryloxy-3α-tert-butyldiphenylsilyloxy-17β-[3-(4(S)-hydroxy-3,4,5,6-tetrahydro-2H-pyran-2-on-6(S)-yl)-2(R)-2-propyl]-5β-androstane 7(R)-7-[[3α-tert-butyldiphenylsilyloxy-12α-(2,2-dimethyl)butyryloxy]-5β-androstan-17β-yl]-3,5-dihydroxyoctanoic acid (0.39 g) is dissolved in methylene chloride (2.5 ml) and the solution cooled to 0° C. Triethylamine (0.077 ml) is added to the solution followed by ethyl chloroformate (0.285 ml). After stirring for about 15 minutes, the mixture is diluted with ether, washed with saturated sodium bicarbonate, brine, dried over magesium sulfate, filtered, and concentrated in vacuo. The crude product is purified by flash chromatography in 70% ether in hexanes to give the desired product as a 50:50 mixture of the 4(R)6(R) and 4(S)6(S) isomers.

Step 10: Preparation of Preparation of 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androstane and 12α-(2,2-dimethyl)butyryloxy-3α-hydroxy-17β-[3-(4(S)-hydroxy-3,4,5,6-tetrahydro-2H-pyran-2-on-6(S)-yl)-2(R)-2-propyl]-5β-androstane A solution of the mixture from Step 9 of 12α-(2,2-dimethyl)butyryloxy-3α-tert-butyldiphenylsilyloxy-17β-[3-(4(R)-hydroxy-3,4,5,6-tetrahydro-2H-pyran-2-on-6(R)-yl)-2(R)-2-propyl]-5β-androstane and 12α-(2,2-dimethyl)butyryloxy-3α-tert-butyldiphenylsilyloxy-17β-[3-(4(S)-hydroxy-3,4,5,6-tetrahydro-2H-pyran-2-on-6(S)-yl)-2(R)-2-propyl]-5β-androstane (0.10 g) in tetrahydrofuran (0.80 ml) is cooled to 0° C. and hydrogen fluoride-pyridine (~70% HF, 0.30 ml) is added. The solution is warmed to room temperature, stirred for about 45 minutes, diluted with ethyl acetate, washed with saturated sodium carbonate, brine, dried over magnesium sulfate, filtered, and concentrated in vacuo. The crude product is purified by flash chromatography in ether to give the desired product as a 1:1 mixture of the 4(R)6(R) and 4(S)6(S) isomers.

EXAMPLE 3

Preparation of 7α-acetoxy-12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androstane and 12α-(2,2-dimethyl)butyryloxy-3α-hydroxy-17β-[3-(4(S)-hydroxy-3,4,5,6-tetrahydro-2H-pyran-2-on-6(S)-yl)-2(R)-2-propyl]-5β-androstane Step 1: Preparation of methyl cholate Using essentially the procedure of Example 1, Step 1, the desired compound is prepared from cholic acid.

Step 2: Preparation of 4(R)-methyl-4-[(3α,7α-di-tert-butyldimethylsilyloxy-12α-hydroxy)-5β-androstan-17β-yl]pentanoate To a solution of methyl cholate (19.9 g) in anhydrous dimethylformamide (50 ml) is added imidazole (7.02 g), tert-butyldimethylsilyl chloride (14.8 g) and 4-dimethylaminopyridine and the mixture stirred at 90° C. for about 18 hours. The mixture is diluted with ethyl acetate and water, and the organic layer is washed with water, brine, dried over magnesium sulfate, filtered and concentrated in vacuo. The crude product is purified by flash chromatography in 5% ethyl acetate in hexane to give the desired product.

Step 3: Preparation of 4(R)-methyl-4-[(12α-benzyloxymethoxy-3α,7α-di-tert-butyldimethylsilyloxy)-5β-androstan-17β-yl]pentanoate A mixture of 4(R)-methyl-4-[(3α,7α-di-tert-butyldimethylsilyloxy-12α-hydroxy)-5β-androstan-17β-yl]pentanoate (21.4 g), benzyl chloromethyl ether (7.73 g) and N,N-diisopropylethylamine (6.38 g) in acetonitrile (30 ml) is heated at 75° C. for about 20 hours, cooled and diluted with ether. The organic solution is washed with water, dried over magnesium sulfate, filtered, and concentrated in vacuo. The crude product is purified by flash chromatography in 5% ethyl acetate in hexane to give the desired product.

Step 4: Preparation of 12α-benzyloxymethoxy-3α,7α-di-tert-butyldimethylsilyloxy-17β-[(1,1-diphenyl)-1-pentanol-4(R)-yl]-5β-androstane A mixture of 3M phenylmagnesium bromide in ether (6.5 ml) and 4(R)-methyl-4-[(12α-benzyloxymethoxy-3α,7α-di-tert-butyldimethylsilyloxy)-5β-androstan-17β-yl]pentanoate (5.0 g) in ether (15 ml) is stirred at 0° C. for about 20 minutes, quenched with 0.1M hydrochloric acid, diluted and the layers separated. The organic layer is washed with saturated ammonium chloride solution, saturated sodium chloride solution, dried over magnesium sulfate, filtered and concentrated in vacuo to give the desired product which is used, without further treatment, for the next step.

Step 5: Preparation of 12α-benzyloxymethoxy-3α,7α-di-tert-butyldimethylsilyloxy-17β-[(1,1-diphenyl)-1-penten-4-yl]-5β-androstane A mixture of 12α-benzyloxymethoxy-3α,7α-di-tert-butyldimethylsilyloxy-17β-[(1,1-diphenyl)-1-pentanol-4(R)-yl]-5β-androstane (6.26 g), triethylamine (4.9 ml) and methanesulfonyl chloride (1.6 ml) in methylene chloride (20 ml) is stirred at room temperature for about 1.5 hours. The mixture is diluted with ether and the organic solution washed with water, dried over magnesium sulfate, filtered, and concentrated in vacuo. The crude product is purified by flash chromatography is 5% ether in hexane to give the desired product.

Step 6: Preparation of 3α,7α,12α-trihydroxy-17β-[(1,1-diphenyl)-1-penten-4-yl]-5β-androstane A mixture of 12α-benzyloxymethoxy-3α,7α-di-tert-butyldimethylsilyloxy-17β-[(1,1-diphenyl)-1-penten-4-yl]-5β-androstane (4.63 g), 1M zinc chloride in ether (10.5 ml) and ethanethiol (2.0 ml) in ether (10 ml) is stirred at room temperature for about 30 minutes. The mixture is concentrated in vacuo and the residue taken up in ether. The ether solution is washed with water, dried over magnesium sulfate, filtered and concentrated in vacuo to give the desired product.

Step 7: Preparation of 3α,7α-diacetoxy-12α-hydroxy-17β-[(1,1-diphenyl)-1-penten-4-yl]-5β-androstane A mixture of 3α,7α,12α-trihydroxy-17β-[(1,1-diphenyl)-1-penten-4-yl]-5β-androstane (2.65 g), acetic anhydride (2.4 ml), and 4-dimethylaminopyridine (0.061 g) in toluene (10 ml) is stirred at room temperature for about 30 minutes, diluted with ether and water and the layers are separated. The organic solution is washed with water, dried over magnesium sulfate, filtered and concentrated in vacuo to give the desired product.

Step 8: Preparation of 3α,7α-diacetoxy-12α-(2,2-dimethyl)butyryloxy-17β-[(1,1-diphenyl)-1-penten-4-yl]-5β-androstane A mixture of 3α,7α-diacetoxy-12α-hydroxy-17β-[(1,1-diphenyl)-1-penten-4-yl]-5β-androstane (7.6 g), 4-pyrrolidinopyridine (0.184 g) and 2,2-dimethylbutyryl chloride (2.0 g) in pyridine (40 ml) is heated at 110° C. for about 1 hour, additional 2,2-dimethylbutyryl chloride (2.0 g) is added and heating is continued for about 16 hours. The mixture is cooled, diluted with 20% ether in hexane and the organic solution washed with 1.0M hydrochloric acid, saturated sodium chloride solution, dried over magnesium sulfate, filtered and concentrated in vacuo. The crude product is purified by flash chromatography in 30% ether in hexane to give the desired product.

Step 9: Preparation of 3-[[3α,7α-diacetoxy-12α-(2,2-dimethyl)butyryloxy]-5β-androstan-17β-yl]butanoic acid To a mixture of 3α,7α-diacetoxy-12α-(2,2-dimethyl)butyryloxy-17β-[(1,1-diphenyl)-1-penten-4-yl]-5β-androstane (6.70 g) and sodium periodate (6.03 g) in carbon tetrachloride (28 ml), acetonitrile (28 ml) and water (47 ml) is added ruthenium(III) chloride hydrate (0.066 g) and the mixture is stirred vigorously at room temperature for about 2.5 hours. The mixture is diluted with ether and water, the layers are separated and the aqueous back-extracted with ether. The combined organic solution is dried over magnesium sulfate, filtered, and concentrated in vacuo. The crude product is purified by flash chromatography in a gradient of 20–50% ether in hexane to give the desired product.

Step 10: Preparation of 3-[[3α,7α-diacetoxy-12α-(2,2-dimethyl)butyryloxy]-5β-androstan-17β-yl]butanol Using essentially the procedure of Example 2, Step 4, and purifying the crude product by flash chromatography in a gradient of 30–35% ethyl acetate in hexane, the desired product is prepared from 3-[[3α,7α-diacetoxy-12α-(2,2-dimethyl)butyryloxy]-5β-androstan-17β-yl]butanoic acid.

Step 11: Preparation of 3-[[3α,7α-diacetoxy-12α-(2,2-dimethyl)butyryloxy]-5β-androstan-17β-yl]butanal Using essentially the procedure of Example 2, Step 5, and purifying the crude product by flash chromatography in 25% ethyl acetate in hexane, the desired product is prepared from 3-[[3α,7α-diacetoxy-12α-(2,2-dimethyl)butyryloxy]-5β-androstan-17β-yl]butanol.

Step 12: Preparation of 7(R)-methyl-7-[[3α,7α-diacetoxy-12α-(2,2-dimethyl)butyryloxy]-5β-androstan-17β-yl]-5-hydroxy-3-oxooctanoate Using essentially the procedure of Example 2, Step 6, the desired product is prepared from 3-[[3α,7α-diacetoxy-12α-(2,2-dimethyl)butyryloxy]-5β-androstan-17β-yl]butanal.

Step 13: Preparation of 7(R)-methyl-7-[[3α,7α-diacetoxy-12α-(2,2-dimethyl)butyryloxy]-5β-androstan-17β-yl]3,5-dihydroxyoctanoate Using essentially the procedure of Example 2, Step 7, and purifying the crude product by flash chromatography in 40% ethyl acetate in hexane, the desired product is prepared from 7(R)-methyl-7-[[3α,7α-diacetoxy-12α-(2,2-dimethyl)butyryloxy]-5β-androstan-17β-yl]-5-hydroxy-3-oxooctanoate.

Step 14: Preparation of 7(R)-7-[[7α-acetoxy-12α-(2,2-dimethyl)butyryloxy]-3α-hydroxy-5β-androstan-17β-yl]-3,5-dihydroxyoctanoic acid Using essentially the procedure of Example 2, Step 8, the desired product is prepared from 7(R)-methyl-7-[[3α,7α-diacetoxy-12α-(2,2-dimethyl)butyryloxy]-5β-androstan-17β-yl]-3,5-dihydroxyoctanoate.

Step 15: Preparation of 7α-acetoxy-12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androstane and 7α-acetoxy-12α-(2,2-dimethyl)butyryloxy-3α-hydroxy-17β-[3-(4(S)-hydroxy-3,4,5,6-tetrahydro-2H-pyran-2-on-6(S)-yl)-2(R)-2-propyl]-5β-androstane Using essentially the procedure of Example 2, Step 9, and purifying the crude product by flash chromatography in 75% ethyl acetate in hexane, the desired product, as a mixture of 4(R)6(R) and 4(S)6(S) isomers, is prepared from 7(R)-7-[[7α-acetoxy-12α-(2,2-dimethyl)butyryloxy]-3α-hydroxy-5β-androstan-17β-yl]-3,5-dihydroxyoctanoic acid.

EXAMPLE 4

Preparation of
12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androst-8(14)ene and
12α-(2,2-dimethyl)butyryloxy-3α-hydroxy-17β-[3-(4(S)-hydroxy-3,4,5,6-tetrahydro-2H-pyran-2-on-6(S)-yl)-2(R)-2-propyl]-5β-androst-8(14)-ene

Step 1: Preparation of 3α,12α-dihydroxy-5β-chol-8(14)-en-24-oic acid

A mixture of cholic acid (11.4 g) and zinc chloride (13 g) in acetone (50 ml) is heated so as to distil off solvent, then heated at an external temperature of 110° C. for about 1.5 hours. The mixture is poured into water, extracted with ether and the organic solution dried over magnesium sulfate, dried, filtered, and concentrated in vacuo. The crude is purified by flash chromatography to give the desired product.

Step 2: Preparation of 3α,12α-dihydroxy-5β-chol-8(14)-en-24-ol

A mixture of lithium aluminum hydride (6.7 g) in tetrahydrofuran (50 ml) is cooled to 0° C. and a solution of 3α, 12α-dihydroxy-5β-chol-8(14)-en-24-oic acid (15.3 g) in tetrahydrofuran (350 ml) is added to dropwise. The mixture is warmed to room temperature, stirred for about 17 hours, and quenched by dropwise addition of water (6.7 ml), 15% sodium hydroxide solution (6.7 ml), and water (6.7 ml). The mixture is filtered, washing the alumina salts with 20% ethanol in ethyl acetate, and the filtrate concentrated in vacuo to give the desired product which is used, without further treatment, for the next step.

Step 3: Preparation of 3α, 12α-dihydroxy-5β-chol-8(14)-en-24-yl p-toluenesulfonate A solution of 3α, 12α-dihydroxy-5β-chol-8(14)-en-24-ol (12.8 g) in methylene chloride/acetonitrile (1:1) (180 ml) is cooled to −5° C. Triethylamine (6 ml), 4-dimethylaminopyridine (0.435 g), and p-toluenesulfonyl chloride (6.65 g) are added and the solution stirred at 0° to 4° C. for about 18 hours. The solution is diluted with ethyl acetate/methanol (9:1), washed with brine and the organic solution dried over magnesium sulfate, filtered, and concentrated in vacuo. The crude product is purified by flash chromatography in ether, followed by 10% methanol in ethyl acetate to give the desired product.

Step 4: Preparation of 3α, 12α-dihydroxy-24-(4-chloro)phenylseleno-5β-chol-8(14)-ene To a mixture of bis(4-chlorophenyl)diselenide (4.0 g) in ethanol (60 ml) is added sodium borohydride, in portions of 0.5 g, until a colorless solution is obtained. 3α, 12α-dihydroxy-5β-chol-8(14)-en-24-yl p-toluenesulfonate (9.28 g) in ethanol (40 ml) is added to the solution which is stirred for about 1 hour at room temperature and diluted with ether. The organic solution is washed with water, dried over magnesium sulfate, filtered, and concentrated in vacuo. The crude product is purified by flash chromatography in 70% ether in hexane to give the desired product.

Step 5: Preparation of 3α-acetoxy-12α-hydroxy-24-(4-chloro)phenylseleno-5β-chol-8(14)-ene Using essentially the procedure of Example 3, Step 7, the desired product is prepared from 3α, 12α-dihydroxy-24-(4-chloro)phenylseleno-5β-chol-8(14)-ene.

Step 6: Preparation of 3α-acetoxy-12α-(2,2-dimethyl)butyryloxy-24-(4-chloro)phenylseleno-5β-chol-8(14)-ene Using essentially the procedure of Example 2, Step 2, and purifying the crude product in 20% ether in hexane, the desired product is prepared from 3α-acetoxy-12α-hydroxy-24-(4-chloro)phenylseleno-5β-chol-8(14)-ene.

Step 7: Preparation of 3α-acetoxy-12α-(2,2-dimethyl)butyryloxy-5β-chola-8(14),23-diene A solution of 3α-acetoxy-12α-(2,2-dimethyl)butyryloxy-24-(4-chloro)phenylseleno-5β-chol-8(14)-ene (4.4 g) in methylene chloride (30 ml) is cooled to −78° C. and 80% m-chloroperbenzoic acid (1.71 g) is added. The mixture is stirred for about 45 minutes and diluted with carbon tetrachloride (20 ml). The mixture is added to a refluxing solution of triethylamine (10 ml) in carbon tetrachloride (160 ml) and the resulting solution stirred for about 35 minutes, diluted with ether and washed with water. The organic solution is dried over magnesium sulfate, filtered and concentrated in vacuo. The crude product is purified by flash chromatography in 10% ether in hexane to give the desired product.

Step 8: Preparation of 3α-acetoxy-12α-(2,2-dimethyl)butyryloxy-5β-chol-8(14)-en-23,24-diol To a mixture of 3α-acetoxy-12α-(2,2-dimethyl)butyryloxy-5β-chola-8(14),23-diene (2.5 g), osmium tetroxide (0.092 g), tert-butyl alcohol (8 ml), and water (2.3 ml) is added 4-methylmorpholine-N-oxide hydrate (0.334 g). The mixture is stirred for about 2 hours at room temperature, diluted with 20% ethyl acetate in ether and washed with aqueous sodium bisulfite. The organic solution is dried over magnesium sulfate, filtered and concentrated in vacuo to give the desired product which is used, without further treatment, for the next step.

Step 9: Preparation of 3(R)-3-[[3α-acetoxy-12α-(2,2-dimethyl)butyryloxy]-5β-androst-8(14)en-17β-yl]butanal To a mixture of 3α-acetoxy-12α-(2,2-dimethyl)butyryloxy-5β-chol-8(14)-en-23,24-diol (2.67 g) in tetrahydrofuran (15 ml) and water (3.0 ml) is added sodium periodate (1.1 g). The mixture is stirred at room temperature for about 45 minutes, diluted with ether and washed with water. The organic solution is dried over magnesium sulfate, filtered, concentrated in vacuo, and the crude product purified by flash chromatography in 20% ether in hexane to give the desired product.

Step 10: Preparation of 7(R)-methyl-7-[[3α-acetoxy-12α-(2,2-dimethyl)butyryloxy]-5β-androst-8(14)en-17β-yl]-5-hydroxy-3-oxooctanoate Using essentially the procedure of Example 2, Step 6, the desired product is prepared from 3(R)-3-[[3α- acetoxy-12α-(2,2-dimethyl)butyryloxy]-5β-androst-8(14)en-17β-yl]butanal.

Step 11: Preparation of
7(R)-methyl-7-[[3α-acetoxy-12α-(2,2-dimethyl)-butyryloxy]-5β-androst-8(14)en-17β-yl]-3,5-dihydroxyoctanoate Using essentially the procedure of Example 2, Step 7, and purifying the crude product by flash chromatography in 70% ether in hexane, the desired product is prepared from 7(R)-methyl-7-[[3α-acetoxy-12α-(2,2-dimethyl)butyryloxy]-5β-androst-8(14)en-17β-yl]-5-hydroxy-3-oxooctanoate.

Step 12: Preparation of
7(R)-7-[[12α-(2,2-dimethyl)butyryloxy]-3α-hydroxy-5β-androst-8(14)en-17β-yl]-3,5-dihydroxyoctanoic acid A mixture of 7(R)-methyl-7-[[3α-acetoxy-12α-(2,2-dimethyl)butyryloxy]-5β-androst-8(14)en-17β-yl]-3,5-dihydroxyoctanoate (1.28 g) and lithium hydroxide hydrate (0.168 g) in methanol (2 ml), water (2 ml) and tetrahydrofuran (2 ml) is stirred at room temperature for about 1.5 hours, quenched with 1M hydrochloric acid (4 ml), and extracted with ethyl acetate. The organic solution is washed with brine, dried over magnesium sulfate, filtered, and concentrated in vacuo. Benzene is azeotroped from the crude product which is then used, without further treatment, for the next step.

Step 13: Preparation of
12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androst-8(14)ene and
12α-(2,2-dimethyl)butyryloxy-3α-hydroxy-17β-[3-(4(S)-hydroxy-3,4,5,6-tetrahydro-2H-pyran-2-on-6(S)-yl)-2(R)-2-propyl]-5β-androst-8(14)-ene A mixture of the crude 7(R)-7-[[12α-(2,2-dimethyl)butyryloxy]-3α-hydroxy-5β-androst-8(14)en-17β-yl]-3,5-dihydroxyoctanoic acid from Step 12, and triethylamine (0.31 ml) in methylene chloride (10 ml) is cooled to 0° C. and 1M ethyl chloroformate in methylene chloride (2 ml) is added. The solution is stirred for about 15 minutes, diluted with ether and washed with brine. The organic solution is dried over magnesium sulfate, filtered, and concentrated in vacuo. The crude product is flash chromatographed in a gradient of 80–100% ether in hexane to give the desired product as a 1:1 mixture of the 4(R)6(R) and 4(S)6(S) isomers.

EXAMPLE 5

Preparation of
12α-(2,2-dimethyl)butyryloxy-3α-hydroxy-17β-[2-(4(R)-hydroxy-3,4,5,6-tetrahydro-2H-pyran-2-on-6(R)-yl)-ethyl]-5β-androst-8(14)-ene Step 1: Preparation of
17β-acetyl-3α,7α,12α-triacetoxy-5β-androstane Using essentially the procedure of Example 1, Steps 1 through 6, the desired product was prepared from cholic acid.

Step 2: Preparation of
17β-acetyl-3α,7α,12α-trihydroxy-5β-androstane

A mixture of 17β-acetyl-3α,7α,12α-triacetoxy-5β-androstane (9.48 g) and lithium hydroxide monohydrate (4.0 g) in methanol (20 ml), water (20 ml) and tetrahydrofuran (20 ml) is stirred at room temperature for about 19 hours, concentrated in vacuo, diluted with ethyl acetate and washed with brine. The organic solution is dried over magnesium sulfate, filtered, and concentrated in vacuo. The crude is purified by flash chromatography in ethyl acetate to give the desired product.

Step 3: Preparation of
17β-acetyl-3α,12α-dihydroxy-5β-adrost-8(14)-ene

17β-acetyl-3α,7α,12α-trihydroxy-5β-androstane (6.12 g) and zinc chloride (9.0 g) are combined in acetone (50 ml). The acetone is distilled off and the residue heated at 110° C. for about 1 hour, additional zinc chloride (3.0 g) is added, and heating continued for about 25 minutes. The mixture is poured into water, extracted with ether, and the ether solution is dried over magnesium sulfate, filtered and concentrated in vacuo. The crude product is purified by flash chromatography in a gradient of 80–100% ether in hexane to give the desired product.

Step 4: Preparation of
17β-acetyl-3α-tert-butyldiphenylsilyloxy-12α-trimethylsilyloxy-5β-adrost-8(14)-ene To a mixture of 17β-acetyl-3α,12α-dihydroxy-5β-adrost-8(14)-ene (2.46 g) and imidazole (0.576 g) in dimethylformamide (20 ml) is added 4-dimethylaminopyridine (0.094 g) and tert-butylchlorodiphenylsilane (2.1 ml) and the resulting mixture is stirred at room temperature for about 4 hours. Imidazole (1.3 g) and trimethylsilyl chloride (2.0 ml) are added to the mixture and stirring continued for about 14 hours at 50° C. The mixture is diluted with ether and washed with dilute sodium bicarbonate solution. The organic solution is dried over magnesium sulfate, filtered, concentrated in vacuo and the crude product purified by flash chromatography in 10% ether in hexane to give the desired product.

Step 5: Preparation of
3α-tert-butyldiphenylsilyloxy-17β-[2-(methoxycarbonyl)ethynyl]-12α-trimethylsilyloxy-5β-adrost-8(14)-ene A solution of diisopropylamine (0.264 ml) in tetrahydrofuran (3.0 ml) is cooled to −15° C. and 2.5M n-butyllithium in hexane (0.68 ml) is added dropwise. The solution is cooled to −78° C. and 17β-acetyl-3α-tert-butyldiphenylsilyloxy-12α-trimethylsilyloxy-5β-adrost-8(14)-ene (1.0 g) in tetrahydrofuran (1.0 ml) is added dropwise, followed by stirring for about 30 minutes, addition of diethylchlorophosphate (0.247 ml), stirring for about 5 minutes and warming to room temperature. This solution is added to a solution of lithium diisopropyl amide (which is prepared as above from diisopropylamine (0.66 ml) and n-butyllithium (1.7 ml of 2.5M)) at −78° C. and the resulting is allowed to warm slowly to room temperature over about 4 hours. The solution is cooled to −78° C. and methyl chloroformate (0.602 ml) is added. After stirring for about 15 minutes, the reaction is quenched with aqueous ammonium chloride and diluted with ether. The organic solution is washed with water, dried over magnesium sulfate, filtered, and concentrated in vacuo. The crude product is purified by flash chromatography in 10% ether in hexane to give the desired product.

Step 6: Preparation of 3α-tert-butyldiphenylsilyloxy-12α-hydroxy-17β-[2-(methoxycarbonyl)ethyl]-5β-adrost-8(14)-ene A mixture of 3α-tert-butyldiphenylsilyloxy-17β-[2-(methoxycarbonyl)ethynyl]-12α-trimethylsilyloxy-5β-adrost-8(14)-ene (0.784 g) and 5% palladium on carbon (0.10 g) in ethyl acetate (5 ml) is stirred under hydrogen at atmospheric pressure at room temperature for about 16 hours. The mixture is filtered and concentrated in vacuo to give the desired product.

Step 7: Preparation of 3α-tert-butyldiphenylsilyloxy-12α-(2,2-dimethyl)-butyryloxy-17β-[2-(methoxycarbonyl)ethyl]-5β-adrost-8(14)-ene Using essentially the procedure of Example 2, Step 2, and purifying the crude product by flash chromatography in 10% ether in hexane, the desired product is prepared from 3α-tert-butyldiphenylsilyloxy-12α-hydroxy-17β-[2-(methoxycarbonyl)ethyl]-5β-adrost-8(14)-ene.

Step 8: Preparation of 3-[[3α-tert-butyldiphenylsilyloxy-12α-(2,2-dimethyl)-butyryloxy]-5β-adrost-8(14)-en-17β-yl]propanol A solution of 3α-tert-butyldiphenylsilyloxy-12α-(2,2-dimethyl)butyryloxy-17β-[2-(methoxycarbonyl)ethyl]-5β-adrost-8(14)-ene (1.21 g) in tetrahydrofuran (3 ml) is cooled to −40° C. and 1.0M lithium triethylborohydride in tetrahydrofuran (3.6 ml) is added dropwise. The solution is stirred for about 20 minutes, quenched with 30% hydrogen peroxide (2 ml) and diluted with ether. The organic solution is washed with water, saturated sodium carbonate, dried over magnesium sulfate, filtered, and concentrated in vacuo. The crude product is purified by flash chromatography in 50% ether in hexane to give the desired product.

Step 9: Preparation of 3-[[3α-tert-butyldiphenylsilyloxy-12α-(2,2-dimethyl)-butyryloxy]-5β-adrost-8(14)-en-17β-yl]propanal A mixture of 3-[[3α-tert-butyldiphenylsilyloxy-12α-(2,2-dimethyl)butyryloxy]-5β-adrost-8(14)-en-17β-yl]propanol (0.957 g) and 4Å molecular sieves (2.0 g) in methylene chloride (14 ml) is stirred for about 15 minutes, 4-methylmorpholine-N-oxide (0.276 g) is added, stirring is continued for about 15 minutes, tetrapropylammonium perruthenate (0.015 g) is added and stirring continued for about 30 minutes. The mixture is diluted with ether, filtered and concentrated in vacuo to give the desired product which is used, without further treatment, for the next step.

Step 10: Preparation of (3R)-[(2S)-(1-hydroxy-1,1,2-triphenyl)-2-ethyl]-5-[[3α-tert-butyldiphenylsilyloxy-12α-(2,2-dimethyl)butyryloxy]-5β-adrost-8(14)-en-17β-yl]-3-hydroxypentanoate To a solution of (S)-2-acetoxy-1,1,2-triphenylethanol (0.52 g) in tetrahydrofuran (1 ml) at −78° C. is added a solution of lithium diisopropyl amide (prepared from diisopropylamine (0.444 ml) and 2.5M n-butyllithium (1.2 ml) in tetrahydrofuran (4 ml)). The solution is warmed to 0° C. This resulting solution is then added, at −78° C., to a solution of magnesium bromide prepared by combining magnesium turnings (0.076 g) and dibromoethane (0.276 ml) in tetrahydrofuran (2 ml) and ether (2 ml). After stirring for about 45 minutes, 3-[[3α-tert-butyldiphenylsilyloxy-12α-(2,2-dimethyl)-butyryloxy]-5β-adrost-8(14)-en-17β-yl]propanal (0.96 g) in tetrahydrofuran (1 ml) is added, the solution stirred for about 1 hour, then quenched with aqueous ammonium chloride solution. The organic solution is dried over magnesium sulfate, filtered and concentrated in vacuo to give the desired product which is used, without further treatment, for the next step.

Step 11: Preparation of (3R)-methyl-5-[[3α-tert-butyldiphenylsilyloxy-12α-(2,2-dimethyl)butyryloxy]-5β-adrost-8(14)-en-17β-yl]-3-hydroxypentanoate A mixture of the crude product from the previous step and 30% sodium methoxide in methanol (0.14 ml) in methanol (1 ml) is stirred at room temperature for about 15 minutes, acidified with concentrated aqueous ammonium chloride solution and diluted with ether. The organic solution is washed with water, dried over magnesium sulfate, filtered, and concentrated in vacuo. The crude product is purified by flash chromatography in 50% ether in hexane to give the desired product.

Step 12: Preparation of (5R)-tert-butyl-7-[[3α-tert-butyldiphenylsilyloxy-12α-(2,2-dimethyl)butyryloxy]-5β-adrost-8(14)-en-17β-yl]-3-oxo-5-hydroxyheptanoate To a solution of 1.5M lithium diisopropylamide (0.88 ml) in tetrahydrofuran (1 ml) at −78° C. is added tert-butyl acetate (0.19 ml) and the solution stirred at −78° C. for about 10 minutes, allowed to warm −40° C. over about 30 minutes, and (3R)-methyl-5-[[3α-tert-butyldiphenylsilyloxy-12α-(2,2-dimethyl)butyryloxy]-5β-adrost-8(14)-en-17β-yl]-3-hydroxypentanoate (0.329 g) in tetrahydrofuran (0.75 ml) is added dropwise. The solution is stirred for about 1.5 hours, quenched with aqueous ammonium chloride, and diluted with ether. The organic solution is washed with water, dried over magnesium sulfate, filtered and concentrated in vacuo. The crude product is purified by flash chromatography in 50% ether in hexane to give the desired product.

Step 13: Preparation of (3R)(5R)-tert-butyl-7-[[3α-tert-butyldiphenylsilyloxy-12α-(2,2-dimethyl)butyryloxy]-5β-adrost-8(14)-en-17β-yl]-3,5-dihydroxyheptanoate Using essentially the procedure of Example 2, Step 7, and purifying the crude product by flash chromatography in 50% ether in hexane, the desired product is prepared from (5R)-tert-butyl-7-[[3α-tert-butyldiphenylsilyloxy-12α-(2,2-dimethyl)butyryloxy]-5β-adrost-8(14)-en-17β-yl]-3-oxo-5-hydroxyheptanoate.

Step 14: Preparation of 12α-(2,2-dimethyl)butyryloxy-3α-hydroxy-17β-[2-(4(R)-hydroxy-3,4,5,6-tetrahydro-2H-pyran-2-on-6(R)-yl)-ethyl]-5β-androst-8(14)-ene To (3R)(5R)-tert-butyl-7-[[3α-tert-butyldiphenylsilyloxy-12α-(2,2-dimethyl)butyryloxy]-5β-adrost-8(14)-en-17β-yl]-3,5-dihydroxyheptanoate (0.14 g) in tetrahydrofuran (0.5 ml) is added hydrogen fluoride/pyridine (~70% HF) (0.2 ml). The mixture is stirred at room temperature for about 20 minutes, additional HF/pyridine (0.1 ml) is added, stirred for about 20 minutes, a third portion of HF/pyridine (0.1 ml) is added and stirring continued for about 10 minutes. The mixture is poured into saturated sodium carbonate solution (6 ml) and extracted with ethyl acetate. The organic solution is washed with brine, dried over magnesium sulfate, filtered and concentrated in vacuo. The crude product is purified by flash chromatography in 60% ether in hexane, then 100% ether to give the desired product.

EXAMPLE 6

Preparation of
12α-(2,2-dimethyl)butyryloxy-3α-hydroxy-17β-[2-(4(S)-hydroxy-3,4,5,6-tetrahydro-2H-pyran-2H-pyran-2-on-6(S)-yl)-ethyl]-5β-androst-8(14)-ene Using essentially the procedure of Example 5, and substituting (R)-2-acetoxy-1,1,2-triphenylethanol for the (S) isomer in Step 10, the desired product is prepared.

EXAMPLE 7

Preparation of
12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androst-8(14)ene Using essentially the procedure of Example 5, and substituting 3(R)-3-[[3α-acetoxy-12α-(2,2-dimethyl)-butyryloxy]-5β-androst-8(14)ene-17β-yl]butanal for the propanal in Step 10, the desired product is prepared.

EXAMPLE 8

Preparation of
12α-(2,2-dimethyl)butyryloxy-3α-hydroxy-17β-[3-(4(S)-hydroxy-3,4,5,6-tetrahydro-2H-pyran-2-on-6(S)-yl)-2(R)-2-propyl]-5β-androst-8(14)ene Using essentially the procedure of Example 5, and substituting 3(R)-3-[[3α-acetoxy-12α-(2,2-dimethyl)-butyryloxy]-5β-androst-8(14)en-17β-yl]butanal for the propanal in Step 10 and substituting (R)-2-acetoxy-1,1,2-triphenylethanol for the (S) isomer in Step 10, the desired product is prepared.

EXAMPLE 9A

Preparation of
4(R)-tert-butoxycarbonylmethyl-2,2-dimethyl-6(S)-[E-2-(tributylstannyl)ethenyl]-1,3-dioxane

Step 1: Preparation of
E-[(2S)-(1-hydroxy-1,1,2-triphenyl)-2-ethyl]-3(S)-3-hydroxy-5-tributylstannyl-4-pentenoate Using essentially the procedure of Example 5, Step 10, and purifying the crude product by flash chromatography in 40% ether in hexane, the desired product is prepared from E-3-tributylstannylacrolein and (S)-2-acetoxy-1,1,2-triphenylethanol.

Step 2: Preparation of
E-methyl-3(S)-3-hydroxy-5-tributylstannyl-4-pentenoate Using essentially the procedure of Example 5, Step 11, the desired product was prepared from E-[(2S)-(1-hydroxy-1,1,2-triphenyl)-2-ethyl]-3(S)-3-hydroxy-5-tributylstannyl-4-pentenoate, and used, without purification, for the next step.

Step 3: Preparation of E-tert-butyl 5(S)-hydroxy-3-oxo-7-tributylstannyl-6-heptenoate A solution of tert-butyl acetate (5.92 g) in tetrahydrofuran (50 ml) is cooled to −78° C. and 1.5M lithium diisopropylamide in tetrahydrofuran/heptane (60/40) (34 ml) is added. The solution is warmed to −40° C. and a solution of the crude product from the previous step (11.4 g) in tetrahydrofuran (40 ml) is added. The resulting solution stirred at −20° to −40° C. for about 2 hours, cooled to −78° C., another portion of 1.5M lithium diisopropylamide solution added (4.5 ml), and stirring continued for about 15 minutes at −30° C. The mixture is quenched with ammonium chloride solution, diluted with ether, and the organic solution washed with water, brine, dried over magnesium sulfate, filtered, and concentrated in vacuo, to give the desired product which is used, without treatment, for the next step.

Step 4: Preparation of E-tert-butyl 3(R)5(S)-dihydroxy-7-tributylstannyl-6-heptenoate Using essentially the procedure of Example 1A, Step 4, and purifying the crude product by flash chromatography in 20% ethyl acetate in hexane, the desired product was prepared from the crude product from the previous step.

Step 5: Preparation of
4(R)-tert-butoxycarbonylmethyl-2,2-dimethyl-6(S)-[E-2-(tributulstannyl)ethenyl]-1,3-dioxane Using essentially the procedure of Example 1A, Step 5, and purifying the crude product by flash chromatography in 5% ether in hexane, the desired product is prepared from E-tert-butyl 3(R)5(S)-dihydroxy-7-tributylstannyl-6-heptenoate.

EXAMPLE 9

Preparation of
12α-(2,2-dimethyl)butyryloxy-3α-hydroxy-17-[E-2-(4(R)-hydroxy-3,4,5,6-tetrahydro-2H-pyran-2-on-6(S)-yl)ethenyl]-5β-androst-17-ene

Step 1: Preparation of
3α-tert-butyldiphenylsilyloxy-12α-hydroxy-5β-androstan-17-one Using essentially the procedure of Example 2, Step 1, the desired product is prepared from 3α, 12α-dihydroxy-5β-androstan-17-one, and used, without purification, for the next step.

Step 2: Preparation of
3α-tert-butyldiphenylsilyloxy-12α-trimethylsilyloxy-5β-androstan-17-one A solution of 3α-tert-butyldiphenylsilyloxy-12α-hydroxy-5β-androstan-17-one (14.6 g) in ether (75 ml) is cooled to 0° C. and 2,6-lutidine (4.2 ml), trimethylsilyl trifluoromethanesulfonate (4.6 ml) are added and the mixture allowed to warm to room temperature, stirred for about 15 minutes, then diluted with ether. The organic solution was washed with dilute aqueous sodium bicarbonate, water and brine, then dried over magnesium sulfate, filtered, concentrated in vacuo, and the crude product purified by flash chromatography in 15% ether in hexane to give the desired product.

Step 3: Preparation of
3α-tert-butyldiphenylsilyloxy-12α-trimethylsilyloxy-17-trifluoromethylsulfonyloxy-5β-androst-17-ene A solution of 1.0M lithium bis(trimethylsilyl)amide in hexane (23.9 ml) in tetrahydrofuran (60 ml) is cooled to −78° C. and a solution of 3α-tert-butyldiphenylsilyloxy-12α-trimethylsilyloxy-5β-androstan-17-one (10.6 g) in tetrahydrofuran (30 ml) is added. The solution is stirred at −78° C. for 15 minutes, a solution of 1,3-dimethyl-3,4,5,6-tetrahydro-2(1H)-pyrimidinone (15.2 ml) and N-phenyltrifluoromethanesulfonimide (9.16 g) in tetrahydrofuran (15 ml) is added dropwise, the solution stirred for 10 minutes, allowed to warm room temperature and diluted with ether. The solution is washed with water, dried over magnesium, filtered, and concentrated in vacuo. The crude product is purified by flash chromatography in 2% ether in hexane to give the desired product.

Step 4: Preparation of 3α-tert-butyldiphenylsilyloxy-17-[E-2-[(4(R)-tert-butoxycarbonylmethyl-2,2-dimethyl)-1,3-dioxan-6(S)-yl]ethenyl]-12-α-trimethylsilyloxy-5β-androst-17-ene Using essentially the procedure of Example 1, Step 16, and purifying the crude product by flash chromatography in 10% ether in hexane, the desired product is prepared from 3α-tert-butyldiphenylsilyloxy-12α-trimethylsilyloxy-17-trifluoromethylsulfonyloxy-5β-androst-17-ene (0.376 g) and 4(R)-tert-butoxycarbonylmethyl-2,2-dimethyl-6(S)-[E-2-(tributylstannyl)ethenyl]-1,3-dioxane.

Step 5: Preparation of 3α-tert-butyldiphenylsilyloxy-17-[E-2-[(4(R)-tert-butoxycarbonylmethyl-2,2-dimethyl)-1,3-dioxan-6(S)-yl]ethenyl]-12-α-hydroxy-5β-androst-17-ene A solution of 3α-tert-butyldiphenylsilyloxy-17-[E-2-[(4(R)-tert-butoxycarbonylmethyl-2,2-dimethyl)-1,3-dioxan-6(S)-yl]ethenyl]-12-α-trimethylsilyloxy-5β-androst-17-ene (0.338 g) and pyridinium p-toluenesulfonate (0.01 g) in anhydrous methanol (10 ml) is stirred at room temperature for about 15 minutes and diluted with ether. The organic solution is washed with saturated aqueous bicarbonate solution, dried over magnesium sulfate, filtered, concentrated in vacuo, to give the desired product which is used, without further treatment, for the next step.

Step 6: Preparation of 3α-tert-butyldiphenylsilyloxy-17-[E-2-[(4(R)-tert-butoxycarbonylmethyl-2,2-dimethyl)-1,3-dioxan-6(S)-yl]ethenyl]-12-α-(2,2-dimethyl)butyryloxy-5β-androst-17-ene Using essentially the procedure of Example 1, Step 11, and purifying the crude product by flash chromatography in 25% ether in hexane, the desired product is prepared from 3α-tert-butyldiphenylsilyloxy-17-[E-2-[(4(R)-tert-butoxycarbonylmethyl-2,2-dimethyl)-1,3-dioxan-6(S)-yl]ethenyl]-12-α-hydroxy-5β-androst-17-ene.

Step 7: Preparation of E-tert-butyl-7-[[3α-hydroxy-12-α-(2,2-dimethyl)butyryloxy-]5β-androsten-17-yl]-3(R),5(S)-dihydroxy-7-heptenoate Using essentially the procedure from Example 2, Step 10, and purifying the crude product by flash chromatography in 80% ether in hexane, the desired product was prepared from 3α-tert-butyldiphenylsilyloxy-17-[E-2-[(4(R)-tert-butoxycarbonylmethyl-2,2-dimethyl)-1,3-dioxan-6(S)-yl]ethenyl]-12-α-(2,2-dimethyl)-butyryloxy-5β-androst-17-ene.

Step 8: Preparation of 12α-(2,2-dimethyl)butyryloxy-3α-hydroxy-17-[E-2-(4(R)-hydroxy-3,4,5,6-tetrahydro-2H-pyran-2-on-6(R)-yl)ethenyl]-5β-androst-17-ene Using essentially the procedure of Example 1, Step 18, the desired product is prepared from E-tert-butyl-7-[[3α-hydroxy-12-α-(2,2-dimethyl)butyryloxy-]5β-androsten-17-yl]-3(R),5(S)-dihydroxy-7-heptenoate.

The compounds of the present invention are useful as hypocholesterolemic or hypolipidemic agents. It is believed that the compounds exhibit such activity by virtue of their ability to inhibit the biosynthesis of cholesterol through specific competitive inhibition of the enzyme HMG-CoA reductase.

The compounds of this invention can normally be administered orally or parenterally, in the treatment of cardiovascular disorders such as hypercholesterolemia and hyperlipidemia.

The compounds of this invention may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of hypocholesterolemic active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, they are suitably buffered, they are made isotonic with sufficient saline or glucose and sterilized by heating or microfiltration.

The dosage regimen in carrying out the method of this invention is that which insures maximum therapeutic response until improvement is obtained and thereafter the minimum effective level which gives relief. Thus, in general, the dosages are those that are therapeutically effective in lowering the serum cholesterol level in the treatment of hypercholesterolemia. In general, the oral dose may be between about 5 mg/kg and about 500 mg/kg, and the i.v. dose about 1 mg/kg to about 200 mg/kg, bearing in mind, of course, that in selecting the appropriate dosage in any specific case, consideration must be given to the patient's weight, general health, age, and other factors which may influence response to the drug. The drug may be administered orally 1 to 4 times per day, preferably twice daily.

The effectiveness of the compounds of this invention as hypocholesterolemic agents may be determined by the following pharmacologic tests which evaluate the HMG-CoA reductase inhibitory activity of said compounds. The HMGR Screen and Ex Vivo Fasted procedures are standard test procedures; the HMG-CoA reductase inhibitory results generally correlate with the HMG-CoA reductase inhibitory activity found in human patients. The procedures are based on those in the following articles: Kleinsek, et al., "Purification of 3-hydroxy-3-methylgutaryl coenzyme A reductase from rat liver", *Proc. Natl. Acad. Sci. USA*, 74 (4), 1431 (1977); Alberts et al., "Mevinolin: A highly potent competitive inhibitor of hydroxy methyl glutaryl-coenzyme A reductase and a cholesterol-lowering agent", *Proc. Natl. Acad. Sci. USA*, 77, 3951, (1980); Ends et al., "Effects of ML-236B on cholesterol metabolism in mice rats: Lack of hypocholesterolemic activity in normal animals", *Biochimica et Biophysica Acta*, 575, 266 (1979); and Balasubramaniam et al. "Evidence of regulation of 3-hydroxy-3-methylglutarylcoenzyme A reductase activity and cholesterol synthesis in monhepatic tissues of rat", *Proc. Natl. Acad. Sci. USA*, 73, (8), 2564 (1976).

HMGR Screen

Male rats were acclimated to an alternate 12 hours light-dark cycle for a period of 2-3 weeks. The animals, weighing 180-230 g, were fed ad libitum a rat chow containing 2% cholestyramine for 5 days prior to sacrifice at the mid-dark period. Liver microsomes were prepared and HMG-CoA reductase enzyme was solubilized from the microsomes by freeze-thaw manipulation in high ionic strength buffer. The enzyme preparation was stored at $-80°$ C. in 300 $\mu$l portion samples. Prior to use, the enzyme was activated by warming at 37° C. for 30 minutes. A reaction mixture was prepared which consisted of, in a volume of 240 $\mu$l: 0.14M potassium phosphate buffer (pH 7.0); 0.18M KCl; 3.5 mM EDTA; 10 mM dithiothreitol; 0.1 mg/ml BSA; 30,000 cpm of [$^{14}$C] HMG-CoA; 20 $\mu$M HMG-CoA, and 200 $\mu$g of activated enzyme with and without compounds of the present invention (in 10 $\mu$l DMSO). After 5 minutes incubation at 37° C. the reaction was initiated with 0.2 mM NADPH. The final assay volume was 300 $\mu$l. The reaction was then terminated with 100 $\mu$l of 1N HCl. After an additional incubation for 15 minutes at 37° C. to allow for complete lactonization of the product, the mixture was diluted with 3 ml distilled water. The diluted mixture was then poured over a 0.7×1.4 cm column containing 100-200 mesh Bio-Rex ion-exchange resin (chloride form of Bio-Rad) which was equilibrated with distilled water. With this resin the unreacted [$^{14}$C] HMG-CoA was adsorbed and the product [$^{14}$C] mevalonolactone was eluted (80% recovery) directly into scintillation vials. After the addition of 10 ml of Aquasol, radioactivities of the samples were measured in a scintillation counter. Results are reported as % inhibition of the enzyme in the presence of a given concentration of a compound of the present invention as compared with the activity of the enzyme in the absence of said compound, i.e., in the absence of inhibitor.

Ex-Vivo Fasted

Rats of 170-210 g were maintained on a low cholesterol diet for one week prior to use. Compounds of the present invention (identified in the table below) were given orally in 0.5% methocel to fasted (fasted for 16 hours) rats. After one hour the rats were decapitated and their livers removed and transferred to chilled oxygenated Kreb's-Ringer-bicarbonate buffer (pH 7.4). The livers were then chopped into 0.5 mm slices using a McIlwain tissue chopper, and were suspended in the same buffer. Aliquots of the suspension containing 100 mg tissue were pipetted to culture tubes which contained [$^{14}$C] sodium octanoate (2 $\mu$Ci, 3 mM). The tubes were gassed with 95% $O_2/CO_2$, capped and incubated at 37° C. in a shaking water bath at 150 oscillation/min. for two hours. The final assay volume was 1.0 ml. After incubation the reaction was stopped by the addition of 1.0 ml of 15% KOH in ethanol, and the internal standard $^3$H-cholesterol was added. The tubes were recapped and the samples were saponified at 75° C. for two hours with periodic mixing. Subsequently an aliquot was removed for protein analysis using Bio-Rad's standard kit, and the remainder of the saponified samples was extracted with 10 ml of petroleum ether for 30 minutes. The lower aqueous phase was frozen in a dry ice/alcohol mixture and the organic layer was poured into labelled tubes. The ether was then evaporated to dryness and the cholesterol was separated by thin layer chromatography on plastic silica gel plates. After visualization with iodine the cholesterol spots were cut and counted with liquid scintillation fluid. Results are reported as % inhibition of cholesterol synthesis after oral dosing with a given amount of a compound of the present invention (expressed in mg/kg of body weight) compared with cholesterol synthesis in the absence of said compound, i.e., in the absence of inhibitor.

Compounds of the present invention exhibit marked activity in the foregoing tests and are considered useful antihypercholesterolemic agents. Results of testing of compounds of the present invention by the above methods are presented in the table below.

| Compound Tested[1] | Inhibitory Activity HMGR Screen | | % Inhibition[2] Ex Vivo Fasted |
|---|---|---|---|
| | Lactone Form | Ring-opened/ Sodium Salt | |
| Example 2 | 33% at 30 $\mu$M | 50% at 352 nM | |
| Example 3 | 23% at 30 $\mu$M | 21% at 300 nM | |
| Example 4 | 19% at 3 $\mu$M | 50% at 119 nM | |
| Example 1 | 50% at 5.9 $\mu$M | 50% at 228 nM | |
| Example 5 | 50% at 1.6 $\mu$M | 50% at 16.9 nM | 47% at 3 mg/kg, p.o. (Na$^+$ salt) |

[1] Results presented in this table are those for the compounds of the illustrative examples presented above.
[2] % inhibition for the HMGR Screen is that of the enzyme HMG-CoA reductase and in the Ex Vivo Fasted assay is the % inhibition of cholesterol synthesis.

What is claimed is:
1. A compound of the formula

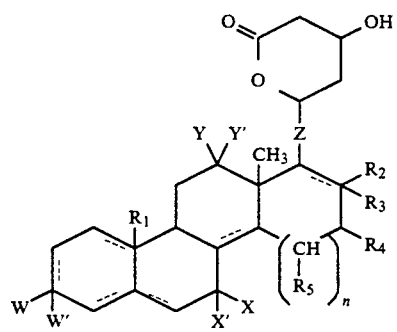

wherein:
R₁ is methyl or part of a double bond;
R₂ is hydrogen, alkyl, aryl or aralkyl;
R₃ is hydrogen, alkyl, or part of a double bond;
R₂ and R₃ together may form a spiro-group of formula

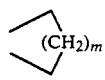

where m is 0-4;
R₄ and R₅ are independently hydrogen, alkyl, aralkyl or aryl;
W is carboalkoxy, carboaryloxy, carboaralkoxy, hydrogen, hydroxy, alkoxy, aryloxy, aralkoxy, alkoxycarbonyloxy, aryloxycarbonyloxy, aralkoxycarbonyloxy, amino, alkylamino, dialkylamino, aminomethyl, alkylaminomethyl, dialkylaminomethyl, alkylthio, alkylsulfonyl, arylthio, arylsulfonyl, alkylsulfonyl, aralkylsulfonyl, alkylsulfinyl, arylsulfinyl aralkylsulfinyl, acyloxy, aroyloxy, acylamino or aroylamino;
W' is hydrogen or part of a double bond;
W and W' together may form an oxo group provided that the A ring of the steroidyl group is not a phenyl ring and provided further that the A ring of the steroidyl group does not contain a double bond in the 2,3 or 3,4 position;
X is carboalkoxy, carboaryloxy, carboaralkoxy, hydrogen, hydroxy, alkoxy, aryloxy, aralkoxy, alkoxycarbonyloxy, aryloxycarbonyloxy, aralkoxycarbonyloxy, amino, alkylamino, dialkylamino, aminomethyl, alkylaminomethyl, dialkylaminomethyl, alkylthio, alkylsulfonyl, arylthio, arylsulfonyl, alkylsulfonyl, aralkylsulfonyl, alkylsulfinyl, arylsulfinyl, aralkylsulfinyl, acyloxy, aroyloxy, acylamino or aroylamino;
X' is hydrogen;
X and X' together may form an oxo group;
Y is carboalkoxy, carboaryloxy, carboaralkoxy, hydrogen, hydroxy, alkoxy, aryloxy, aralkoxy, alkoxycarbonyloxy, aryloxycarbonyloxy, aralkoxycarbonyloxy, amino, alkylamino, dialkylamino, aminomethyl, alkylaminomethyl, dialkylaminomethyl, alkylthio, alkylsulfonyl, arylthio, arylsulfonyl, alkylsulfonyl, aralkylsulfonyl, alkylsulfinyl, arylsulfinyl, aralkylsulfinyl, acylamino, aroylamino or

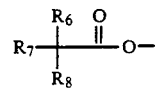

wherein R₆, R₇ and R₈ are independently hydrogen, alkyl, aralkyl or aryl;
Y' is hydrogen;
Y and Y' together may form an oxo group;
Z is

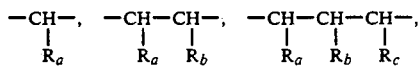

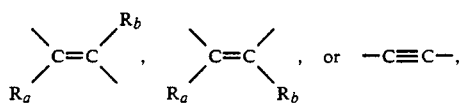

where R$_a$, R$_b$, and R$_c$ are independently hydrogen or lower alkyl; and
wherein the notation ===== on the ring indicates that the bond may be a single or double bond, and
n is 0 or 1.

2. A compound of claim 1 of the formula

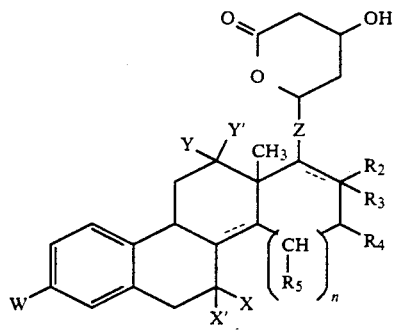

3. A compound of claim 1 of the formula

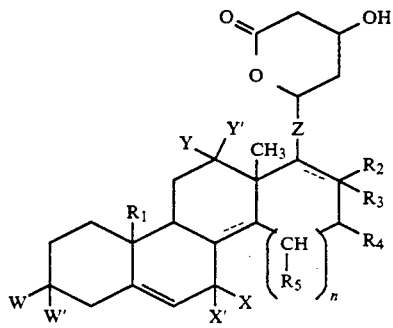

4. A compound of claim 1 of the formula

5. A compound of claim 4 of the formula

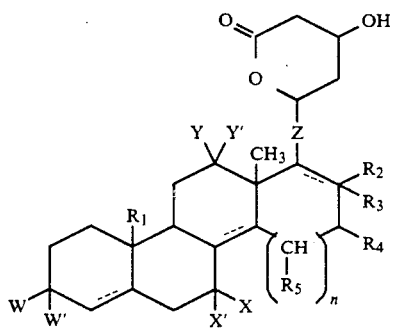

6. A compound of claim 5 of the formula

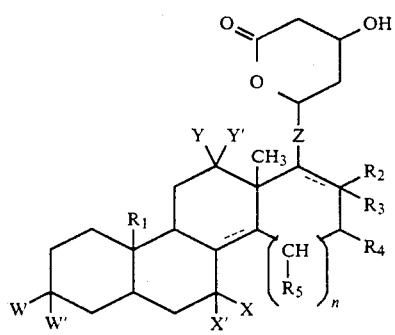

7. A compound of claim 5 of the formula

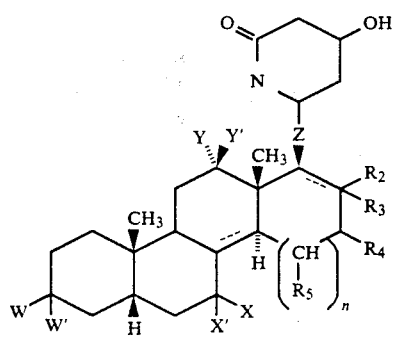

8. A compound of claim 6 of the formula

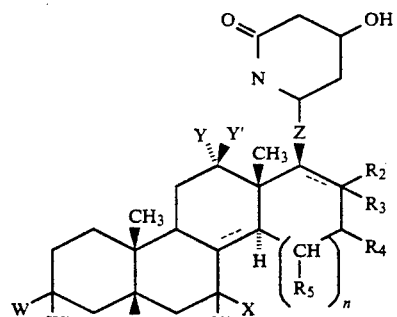

9. A compound of claim 8 wherein
  $R_2$ is hydrogen, alkyl, aryl or aralkyl; and
  $R_3$ is hydrogen, alkyl or part of a double bond.

10. A compound of claim 9 which is 12α-(2,2-dimethyl)butyryloxy-3α-hydroxy-17a-[E-2-(4(R)-hydroxy-3,4,5,6-tetrahydro-2H-pyran-2-on-6(S)-yl)ethenyl]-D-homo-5β-androst-17-ene.

11. A compound of claim 9 which is 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androstane.

12. A compound of claim 9 which is 7α-acetoxy-12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androstane.

13. A compound of claim 9 which is 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]-5β-androst-8(14)ene.

14. A compound of claim 9 which is 12α-(2,2-dimethyl)butyryloxy-3α-hydroxy-17β-[2-(4(R)-hydroxy-3,4,5,6-tetrahydro-2H-pyran-2-on-6(R)-yl)-ethyl]-5β-androst-8(14)-ene.

15. A compound of claim 2 which is 12α-(2,2-dimethyl)butyryloxy-3α-hydroxy-17β-[3-(4(R)-hydroxy-3,4,5,6-tetrahydro-2H-pyran-2-on-6(R)-yl)-2(R)-2-propyl]androst-1,3,5(10)-triene.

16. A compound of claim 3 which is 12α-(2,2-dimethyl)butyryloxy-3α-hydroxy-17β-[2-(4(R)-hydroxy-3,4,5,6-tetrahydro-2H-pyran-2-on-6(R)-yl)-ethyl]androst-5(6)-ene.

17. A compound of claim 7 which is 12α-(2,2-dimethyl)butyryloxy-3α-hydroxy-17β-[2-(4(R)-hydroxy-3,4,5,6-tetrahydro-2H-pyran-2-on-6(R)-yl)-ethyl]-5α-androst-8(14)-ene.

18. A hypocholesterolemic, hypolipidemic pharmaceutical composition comprising a therapeutically effective amount of a compound of claim 1 and a pharmaceutically acceptable carrier.

19. A method of inhibiting cholesterol biosynthesis in a patient in need of such treatment comprising administering a pharmaceutical composition defined in claim 18.

* * * * *